US010857153B2

(12) United States Patent
Wu et al.

(10) Patent No.: US 10,857,153 B2
(45) Date of Patent: Dec. 8, 2020

(54) PYRIMIDINE COMPOUNDS CONTAINING ACIDIC GROUPS

(71) Applicant: Apros Therapeutics, Inc., San Diego, CA (US)

(72) Inventors: Tom Yao-Hsiang Wu, San Diego, CA (US); Andrew T. Miller, San Diego, CA (US)

(73) Assignee: APROS THERAPEUTICS, INC., San Diego, CA (US)

( * ) Notice: Subject to any disclaimer, the term of this patent is extended or adjusted under 35 U.S.C. 154(b) by 0 days.

(21) Appl. No.: 16/429,104

(22) Filed: Jun. 3, 2019

(65) Prior Publication Data

US 2019/0365756 A1 Dec. 5, 2019

Related U.S. Application Data

(60) Provisional application No. 62/680,324, filed on Jun. 4, 2018.

(51) Int. Cl.

| | |
|---|---|
| ***C07D 403/10*** | (2006.01) |
| ***A61K 31/506*** | (2006.01) |
| ***A61P 35/04*** | (2006.01) |
| ***A61K 9/00*** | (2006.01) |
| ***A61K 31/505*** | (2006.01) |
| ***A61K 47/38*** | (2006.01) |
| ***C07D 239/48*** | (2006.01) |

(52) U.S. Cl.

CPC .......... *A61K 31/506* (2013.01); *A61K 9/0073* (2013.01); *A61K 31/505* (2013.01); *A61K 47/38* (2013.01); *A61P 35/04* (2018.01); *C07D 239/48* (2013.01); *C07D 403/10* (2013.01)

(58) Field of Classification Search

CPC .................................................... C07D 403/10

See application file for complete search history.

(56) References Cited

U.S. PATENT DOCUMENTS

| | | | |
|---|---|---|---|
| 4,689,338 | A | 8/1987 | Gerster |
| 8,268,990 | B2 | 9/2012 | Bennett et al. |
| 10,287,253 | B2 | 5/2019 | Wu |
| 2018/0155298 | A1 | 6/2018 | Wu |
| 2019/0314372 | A1 | 10/2019 | Wu |

FOREIGN PATENT DOCUMENTS

| | | |
|---|---|---|
| WO | WO 97/22596 | 6/1997 |
| WO | WO 97/30035 | 8/1997 |
| WO | WO 97/32856 | 9/1997 |
| WO | WO 98/01448 | 1/1998 |
| WO | WO 98/13354 | 4/1998 |
| WO | WO 98/35985 | 8/1998 |
| WO | WO 99/02166 | 1/1999 |
| WO | WO 99/28321 | 6/1999 |
| WO | WO 00/40529 | 7/2000 |
| WO | WO 00/41669 | 7/2000 |
| WO | WO 00/47212 | 8/2000 |
| WO | WO 01/32651 | 5/2001 |
| WO | WO 01/60814 | 8/2001 |
| WO | WO 01/92224 | 12/2001 |
| WO | WO 01/94341 | 12/2001 |
| WO | WO 02/04434 | 1/2002 |
| WO | WO 02/08213 | 1/2002 |
| WO | WO 2009/067081 | 5/2009 |
| WO | WO 2010/133885 | 11/2010 |
| WO | WO 2012/031140 | 3/2012 |
| WO | WO 2012/066336 | 5/2012 |
| WO | WO 2013/172479 | 11/2013 |
| WO | WO 2014/128189 | 8/2014 |
| WO | WO 2018/106606 | 6/2018 |
| WO | WO 2019/236496 | 12/2019 |

OTHER PUBLICATIONS

International Search Report and Written Opinion issued by the International Searching Authority for Application No. PCT/US2017/064541, dated Mar. 5, 2018, 17 pages.

International Search Report and Written Opinion issued by the International Searching Authority for Application No. PCT/US2019/035247, dated Jul. 31, 2019, 13 pages.

Streitweiser et al., Flyleaf of "Introduction to Organic Chemistry", MacMillan Publishing Co., Inc., 1976, 4 pages.

Lombardo et al., "Discovery of N-(2-chloro-6-methyl-phenyl)-2-(6-(4-(2-hydroxyethyl)-piperazin-1-yl)-2-methylpyrimidin-4-ylamino)thiazole-5-carboxamide (BMS-354825), a dual Src/Abl kinase with potent antitumor activity in preclinical assays," J. Med. Chem. 47(27): 6658-6661 (2004).

(Continued)

*Primary Examiner* — Brian E McDowell

(74) *Attorney, Agent, or Firm* — Cooley LLP

(57) ABSTRACT

The present disclosure relates to a class of pyrimidine derivatives having immunomodulating properties that act via TLR7 which are useful in the treatment of lung cancer and other respiratory conditions. The present disclosure specifically discloses compounds having the structuree of Formula (I), and pharmaceutically acceptable salts thereof.

(I)

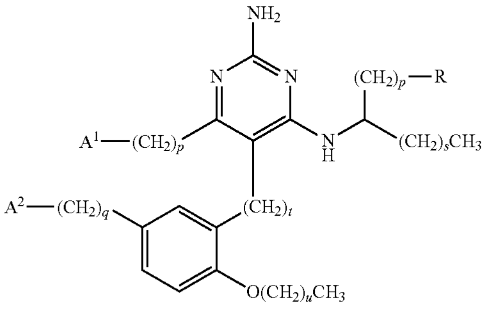

10 Claims, 3 Drawing Sheets

(56) References Cited

OTHER PUBLICATIONS

Oballa et al., "Development of a liver-targeted stearoyl-CoA desaturase (SCD) inhibitor (MK-8245) to establish a therapeutic window for the treatment of diabetes and dyslipidemia," J. Med. Chem. 54(14):5082-5096 (2011).
Pfefferkorn et al., 'Discovery of (S)-6-(3-cyclopentyl-2-(4-(trifluoromethyl)-1H-imidazol-1-yl) propanamido) nicotinic acid as a hepatoselective glucokinase activator clinical candidate for treating type 2 diabetes mellitus, J. Med. Chem., 2012, 55(3):1318-1333 (2012).
Santarpia et al., "Programmed cell death protein-1/programmed cell death ligand-1 pathway inhibition and predictive biomarkers: understanding transforming growth factor-beta role," Transl. Lung Cancer Res 2015; 4(6): 728-742.
Stern et al., "Overview of monoclonal antibodies in cancer therapy: present and promise," Crit Rev Oncol Hematol. 54(1):11-29 (2005).
Tu et al., "Medicinal Chemistry Design Principles for Liver Targeting Through OATP Transporters," Current Topics in Medicinal Chemistry 13(7): 857-866 (2013).
McGowan et al., "Novel Pyrimidine Toll-like Receptor 7 and 8 Dual Agonists to Treat Hepatitis B Virus," J. Med. Chem., Aug. 11, 2016, 59(17):7936-7949.

PYRIMIDINE COMPOUNDS CONTAINING ACIDIC GROUPS

CROSS REFERENCE TO RELATED APPLICATIONS

This application claims the benefit of U.S. Provisional Application No. 62/680,324, filed Jun. 4, 2018, the contents of which are incorporated herein by reference in its entirety.

FIELD OF THE INVENTION

The present disclosure relates to a class of pyrimidine derivatives having immunomodulating properties that act via TLR7 which are useful in the treatment of lung cancer and other respiratory conditions.

BACKGROUND OF THE INVENTION

The present disclosure relates to pyrimidine derivatives, processes for their preparation, pharmaceutical compositions containing them and their use in therapy.

The immune system is comprised of innate and acquired immunity, both of which work cooperatively to protect the host from microbial infections. It has been shown that innate immunity can recognize conserved pathogen-associated molecular patterns through toll-like receptors (TLRs) expressed on the cell surface of immune cells. Recognition of invading pathogens then triggers cytokine production (including interferon alpha(IFNα)) and upregulation of co-stimulatory molecules on phagocytes, leading to modulation of T cell function. Thus, innate immunity is closely linked to acquired immunity and can influence the development and regulation of an acquired response.

TLRs are a family of type I transmembrane receptors characterized by an $NH_2$-terminal extracellular leucine-rich repeat domain (LRR) and a COOH-terminal intracellular tail containing a conserved region called the Toll/IL-1 receptor (TIR) homology domain. The extracellular domain contains a varying number of LRR, which are thought to be involved in ligand binding. Eleven TLRs have been described to date in humans and mice. They differ from each other in ligand specificities, expression patterns, and in the target genes they can induce.

Ligands which act via TLRs (also known as immune response modifiers (IRMS)) have been developed, for example, the imidazoquinoline derivatives described in U.S. Pat. No. 4,689,338 which include the product Imiquimod for treating genital warts, and the adenine derivatives described in WO 98/01448 and WO 99/28321.

Compounds with high aqueous solubility are desirable for inhalation in order to minimize insoluble particulate deposition in lung. Introducing multiple ionizable moieties is one way to enhance the aqueous solubility of low molecular weight molecules by increasing the fraction of ionization. However, the installment of the charged functional groups (e.g. carboxylic acid and its surrogates) must be carefully positioned not to affect the activity of the pharmacophore. There is a need for active TLR7 agonists that are sufficiently water soluble so that they may be administered through inhalation.

SUMMARY OF THE INVENTION

The present disclosure describes novel TLR7 agonists containing two acidic groups strategically positioned on a pyrimidine pharmacophore. These compounds have enhanced solubility compared to the pyrimidine TLR7 agonists containing only one acidic group. Examples of pyrimidine TLR7 agonists containing one acidic group may be found in US 2018/0155298.

The compounds described herein are TLR7 agonists that may be used to treat lung cancers and other respiratory conditions via inhalation administration.

The present disclosure provides a compound having the structure of Formula (I), and pharmaceutically acceptable salts thereof, (I)

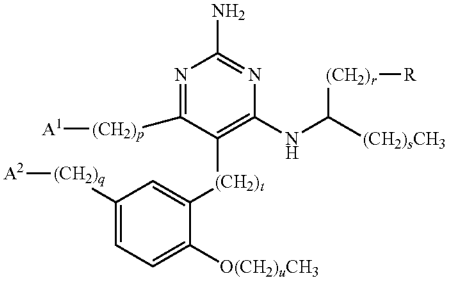

wherein

R is selected from the group consisting of —OH, —$SO_2CH_3$, —$NH_2$, —NHAc, and

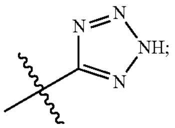 [SMILES: *c1nn[nH]n1]

$A^1$ is selected from the group consisting of

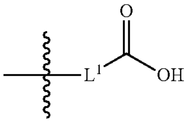,
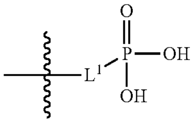,
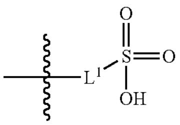,
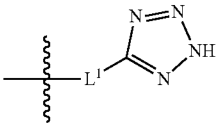,
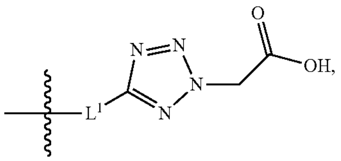
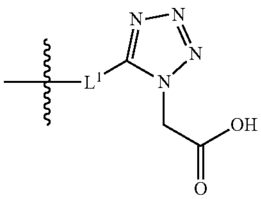, and
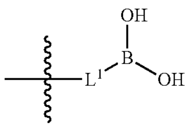;

$A^2$ is selected from the group consisting of

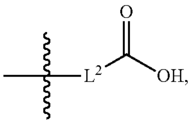

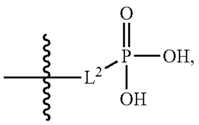

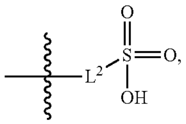

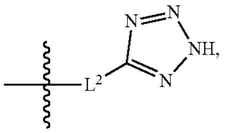

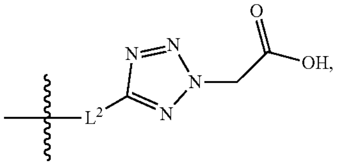

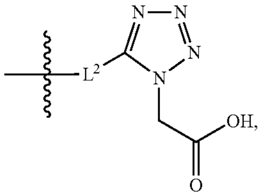

and

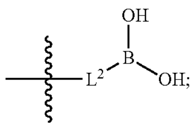

$L^1$ is a bond or $—(CH_2)_m—$;

$L^2$ is a bond or $—(CH_2)_n—$; and m, n, p, q, r, s, t, and u are independently selected from zero to four;

wherein if $A^1(CH_2)_p$ is $—CH_2CH_2C(═O)OH$, $A^2(CH_2)_q$ is $—CH_2C(═O)OH$, r is 2, s is 3, t is 1 and u is 0, then R cannot be $SO_2CH_3$.

The present disclosure provides a compound having the structure of Formula (I), and pharmaceutically acceptable salts thereof, (I)

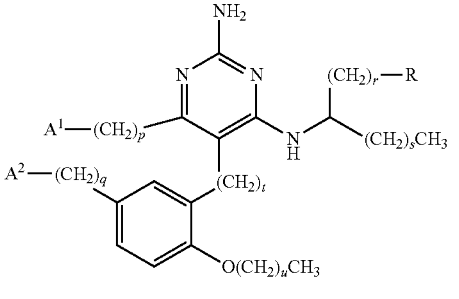

wherein

R is selected from the group consisting of —OH, $—SO_2CH_3$, $—NH_2$, —NHAc, and

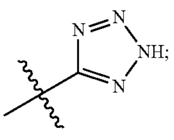 [SMILES: *c1nn[nH]n1]

$A^1$ is selected from the group consisting of

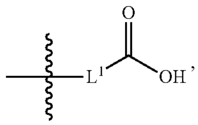

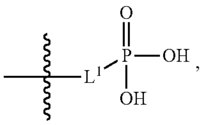

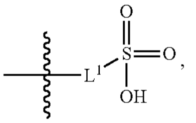

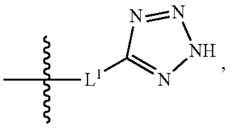

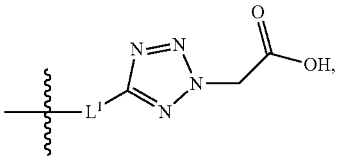

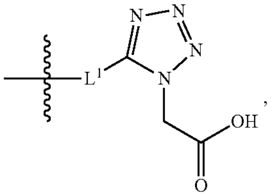

and

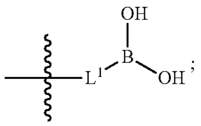

$A^2$ is selected from the group consisting of

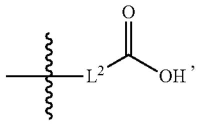

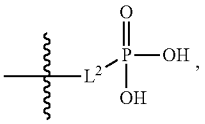

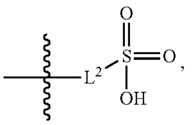

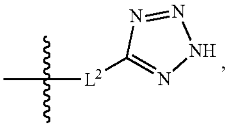

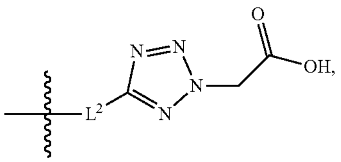

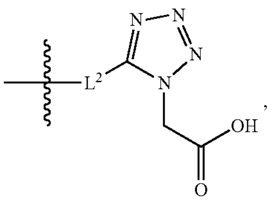

and

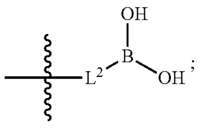

$L^1$ is a bond or $—(CH_2)_m—$;

$L^2$ is a bond or $—(CH_2)_n—$; and m, n, p, q, r, s, t, and u are independently selected from zero to four.

In some embodiments of Formula (I), wherein if $A^1(CH_2)_p$ is $—CH_2CH_2C(═O)OH$, $A^2(CH_2)_q$ is $—CH_2C(═O)OH$, r is 2, s is 3, t is 1 and u is 0, then R is —OH, $—NH_2$, —NHAc, or

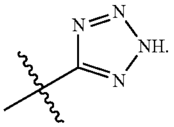 [SMILES: *c1nn[nH]n1]

In some embodiments of Formula (I), wherein if $A^1(CH_2)_p$ is $—CH_2CH_2C(═O)OH$, $A^2(CH_2)_q$ is $—CH_2C(═O)OH$, r is 2, s is 3, t is 1 and u is 0, then R cannot be $SO_2CH_3$.

The present disclosure provides pharmaceutical compositions comprising a compound of the present disclosure, or a pharmaceutically acceptable salt thereof, and a pharmaceutically acceptable carrier.

The present disclosure provides a method of treating a respiratory condition comprising administering to a subject in need thereof an effective amount of a compound of the present disclosure, or a pharmaceutically acceptable salt thereof. In particular embodiments, the respiratory condition is lung cancer.

The present disclosure provides a method of treating a respiratory condition comprising administering to a subject in need thereof an effective amount of a pharmaceutical composition of the present disclosure, or a pharmaceutically acceptable salt thereof. In particular embodiments, the respiratory condition is lung cancer.

The present disclosure provides a use of a compound of the present disclosure, or a pharmaceutically acceptable salt thereof, in the manufacture of a medicament.

The present disclosure provides a compound of the present disclosure, or a pharmaceutically acceptable salt thereof, for use in therapy.

The present disclosure provides a compound of the present disclosure, or a pharmaceutically acceptable salt thereof, for use in treating a respiratory disease. In particular embodiments, the respiratory condition is lung cancer.

The present disclosure provides a pharmaceutical composition for use in therapy.

The present disclosure provides a pharmaceutical composition for use in treating a respiratory disease. In particular embodiments, the respiratory condition is lung cancer.

DETAILED DESCRIPTION

Figure 1:
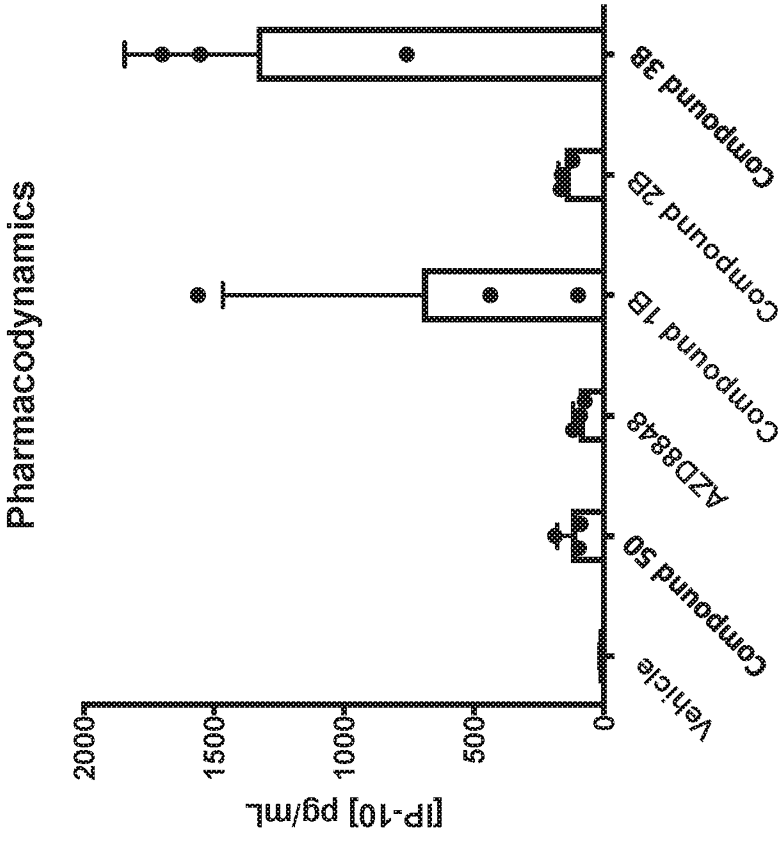
FIG. 1 depicts a bar graph of the mean concentration of IP-10 marker in BALB/C mice after 5 hours from intranasal administration of vehicle, Compound 50, AZD8848, Compound 1A, Compound 2B, or Compound 3B.

Although specific embodiments of the present disclosure are herein illustrated and described in detail, the invention is not limited thereto. The detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

Terms

The following definitions are meant to clarify, but not limit, the terms defined. If a particular term used herein is not specifically defined, such term should not be considered indefinite. Rather, terms are used within their accepted meanings.

As used herein, the term "pharmaceutically acceptable" refers to carrier(s), diluent(s), excipient(s) or salt forms that are compatible with the other ingredients of the formulation and not deleterious to the recipient of the pharmaceutical composition.

As used herein, the term "pharmaceutical composition" refers to a compound of the present disclosure optionally admixed with one or more pharmaceutically acceptable carriers, diluents, excipients, or adjuvants. Pharmaceutical compositions preferably exhibit a degree of stability to environmental conditions so as to make them suitable for manufacturing and commercialization purposes.

As used herein, the terms "effective amount," "therapeutic amount," or "effective dose" refer to an amount of active ingredient sufficient to elicit the desired pharmacological or therapeutic effects, thus resulting in effective prevention or treatment of a disorder. Prevention of a disorder may be manifested by delaying or preventing the progression of the disorder, as well as delaying or preventing the onset of the symptoms associated with the disorder. Treatment of the disorder may be manifested by a decrease or elimination of symptoms, inhibition or reversal of the progression of the disorder, as well as any other contribution to the well-being of the patient.

The effective dose can vary, depending upon factors such as the condition of the patient, the severity of the symptoms of the disorder, and the manner in which the pharmaceutical composition is administered. Typically, to be administered in an effective dose, compounds are required to be administered in an amount of less than 30 mg. Often, the compounds may be administered in an amount from less than about 1 mg weight to less than about 100 μg, and occasionally between about 10 μg to less than 100 μg. In some embodiments, the dose range is between 10-10,000 micrograms per dose. In particular embodiments, the dose range is between 30-100 micrograms per dose, 30-80 micrograms per dose, or 40-75 micrograms per dose. In some embodiments, the dose is 60 micrograms per dose. The foregoing effective doses typically represent that amount administered as a single dose, or as one or more doses administered over a 24 hours period. For human patients, the effective dose of the compounds may require administering the compound in an amount of at least about 1 microgram/24 hr/patient, but not more than about 2400 microgram/24 hr/patient, and often not more than about 500 microgram/24 hr/patient.

Compounds

The present disclosure provides a compound having the structure of Formula (I), or a pharmaceutically acceptable salt thereof, (I)

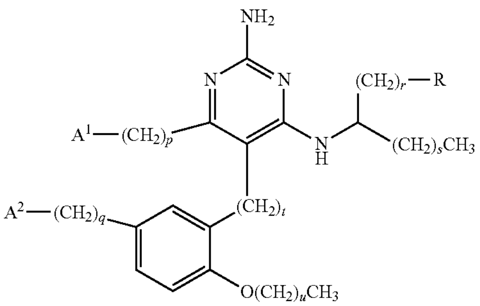

wherein

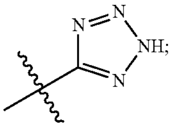 [SMILES: *c1nn[nH]n1]

R is selected from the group consisting of —OH, —$SO_2CH_3$, —$NH_2$, —NHAc, and $A^1$ is selected from the group consisting of

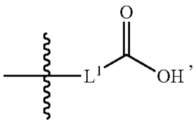, 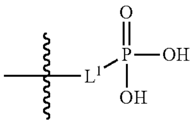, 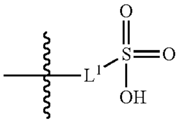, 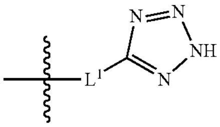, 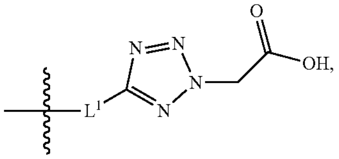 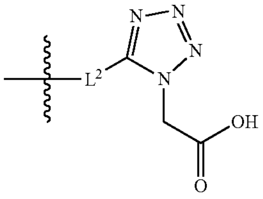, and 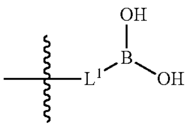;

$A^2$ is selected from the group consisting of

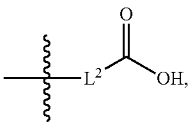 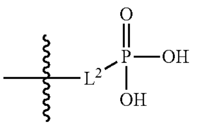, 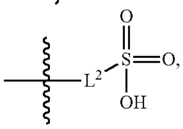 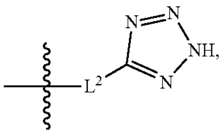

-continued

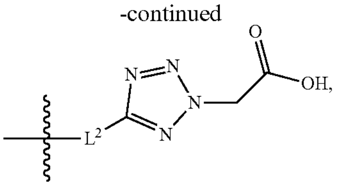 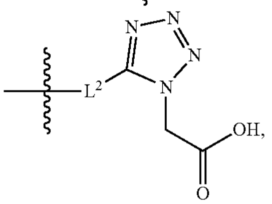 and 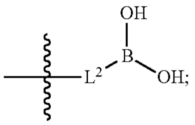

$L^1$ is a bond or —$(CH_2)_m$—;

$L^2$ is a bond or —$(CH_2)_n$—; and m, n, p, q, r, s, t, and u are independently selected from zero to four;

wherein if $A^1(CH_2)_p$ is —$CH_2CH_2C(=O)OH$, $A^2(CH_2)_q$ is —$CH_2C(=O)OH$, r is 2, s is 3, t is 1 and u is 0, then R cannot be $SO_2CH_3$.

The present disclosure provides a compound having the structure of Formula (I), and pharmaceutically acceptable salts thereof, (I)

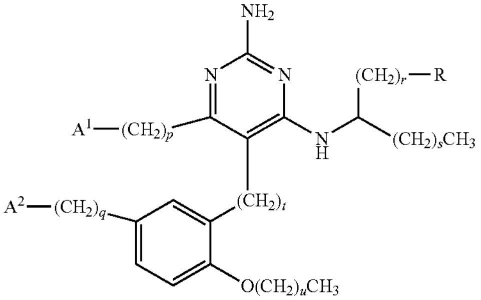

wherein

R is selected from the group consisting of —OH, —$SO_2CH_3$, —$NH_2$, —NHAc, and

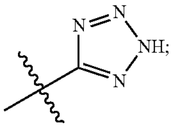 [SMILES: *c1nn[nH]n1]

$A^1$ is selected from the group consisting of

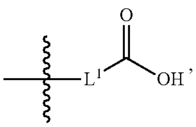, 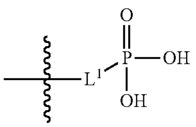, 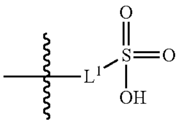, 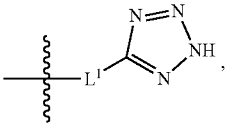,

-continued

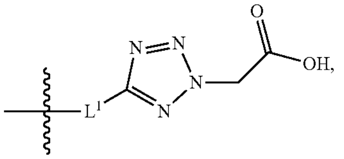

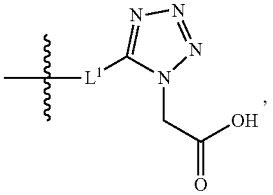

, and

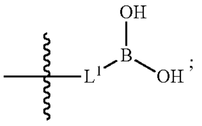

$A^2$ is selected from the group consisting of

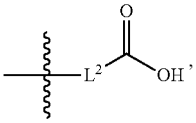

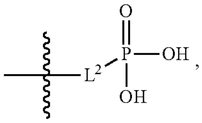

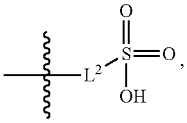

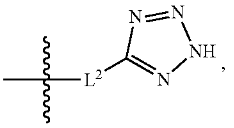

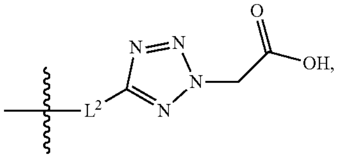

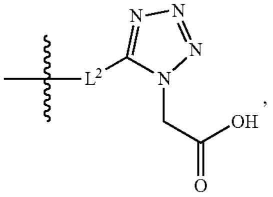

, and

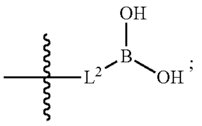

$L^1$ is a bond or $-(CH_2)_m-$;

$L^2$ is a bond or $-(CH_2)_n-$; and m, n, p, q, r, s, t, and u are independently selected from zero to four.

In some embodiments of Formula (I)), wherein if $A^1(CH_2)_p$ is $-CH_2CH_2C(=O)OH$, $A^2(CH_2)_q$ is $-CH_2C(=O)OH$, r is 2, s is 3, t is 1 and u is 0, then R is —OH, $-NH_2$, —NHAc, or

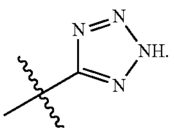 [SMILES: *c1nn[nH]n1]

In some embodiments of Formula (I), wherein if $A^1(CH_2)_p$ is $-CH_2CH_2C(=O)OH$, $A^2(CH_2)_q$ is $-CH_2C(=O)OH$, r is 2, s is 3, t is 1 and u is 0, then R cannot be $SO_2CH_3$.

In some embodiments, the disclosure provides a compound having the structure of Formula (I), or a pharmaceutically acceptable salt thereof, wherein R is selected from the group consisting of —OH and $-SO_2CH_3$. In certain embodiments, R is —OH. In certain embodiments, R is $-SO_2CH_3$.

In some embodiments, the disclosure provides a compound having the structure of Formula (I), or a pharmaceutically acceptable salt thereof, wherein $A^1$ is selected from the group consisting of

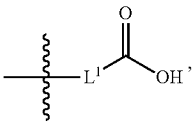

and

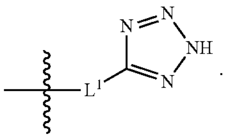

In certain embodiments, $A^1$ is

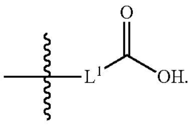

In certain embodiments, $A^1$ is

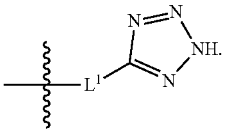

In some embodiments, the disclosure provides a compound having the structure of Formula (I), or a pharmaceutically acceptable salt thereof, wherein $A^2$ is selected from the group consisting of

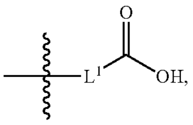

and

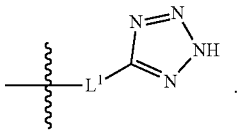

In certain embodiments, $A^2$ is

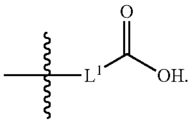

In certain embodiments, $A^2$ is

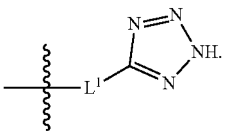

In some embodiments, the disclosure provides a compound having the structure of Formula (I), or a pharmaceutically acceptable salt thereof, wherein $L^1$ is a bond or $-(CH_2)_m-$. In certain embodiments, $L^1$ is a bond. In certain embodiments, $L^1$ is $-(CH_2)_m-$.

In some embodiments, the disclosure provides a compound having the structure of Formula (I), or a pharmaceutically acceptable salt thereof, wherein $L^2$ is a bond or $—(CH_2)_n—$. In certain embodiments, $L^2$ is a bond. In certain embodiments, $L^2$ is $—(CH_2)_n—$.

In some embodiments, the disclosure provides a compound having the structure of Formula (I), or a pharmaceutically acceptable salt thereof, wherein m, n, p, q, r, s, t, and u are independently selected from zero to three. In certain embodiments, m, n, p, q, r, s, t, and u are independently selected from zero to two. In certain embodiments, m, n, p, q, r, s, t, and u are independently selected from one to four. In certain embodiments, m, n, p, q, r, s, t, and u are independently selected from one to three. In certain embodiments, m, n, p, q, r, s, t, and u are independently zero. In certain embodiments, m, n, p, q, r, s, t, and u are independently one. In certain embodiments, m, n, p, q, r, s, t, and u are independently two. In certain embodiments, m, n, p, q, r, s, t, and u are independently three. In certain embodiments, m, n, p, q, r, s, t, and u are independently four.

In some embodiments, the disclosure provides a compound having the structure of Formula (I), or a pharmaceutically acceptable salt thereof, wherein m is zero. In certain embodiments, m is one. In certain embodiments, n is zero. In certain embodiments, n is one. In certain embodiments, m and n are zero. In certain embodiments, m and n are one.

In some embodiments, the disclosure provides a compound having the structure of Formula (I), or a pharmaceutically acceptable salt thereof, wherein p is zero. In certain embodiments, p is one. In certain embodiments, p is two. In certain embodiments, p is three.

In some embodiments, the disclosure provides a compound having the structure of Formula (I), or a pharmaceutically acceptable salt thereof, wherein q is zero. In certain embodiments, q is one. In certain embodiments, q is two. In certain embodiments, q is three.

In some embodiments, the disclosure provides a compound having the structure of Formula (I), or a pharmaceutically acceptable salt thereof, wherein r is zero. In certain embodiments, r is one. In certain embodiments, r is two. In certain embodiments, r is three.

In some embodiments, the disclosure provides a compound having the structure of Formula (I), or a pharmaceutically acceptable salt thereof, wherein s is zero. In certain embodiments, s is one. In certain embodiments, s is two. In certain embodiments, s is three.

In some embodiments, the disclosure provides a compound having the structure of Formula (I), or a pharmaceutically acceptable salt thereof, wherein t is zero. In certain embodiments, t is one. In certain embodiments, t is two. In certain embodiments, t is three.

In some embodiments, the disclosure provides a compound having the structure of Formula (I), or a pharmaceutically acceptable salt thereof, wherein u is zero. In certain embodiments, u is one. In certain embodiments, u is two. In certain embodiments, u is three.

In certain embodiments, the disclosure provides a compound having the structure of Formula (I), or a pharmaceutically acceptable salt thereof, wherein p is 2 and q is 1.

In certain embodiments, the disclosure provides a compound having the structure of Formula (I), or a pharmaceutically acceptable salt thereof, wherein R is —OH or $—SO_2CH_3$.

The present disclosure provides a compound of Formula (I), or a pharmaceutically acceptable salt thereof, having one, two, or three of the following features:

a) R is $—SO_2CH_3$ or —OH;

b) $A^1$ is $—CO_2H$; and c) $A^2$ is

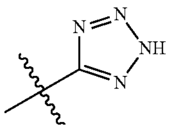 [SMILES: *c1nn[nH]n1]

or $—CO_2H$, wherein if $A^1(CH_2)_p$ is $—CH_2CH_2C(=O)OH$, $A^2(CH_2)_q$ is $—CH_2C(=O)OH$, r is two, s is three, t is one and u is zero, then R cannot be $SO_2CH_3$. In some embodiments, wherein if $A^1(CH_2)_p$ is $—CH_2CH_2C(=O)OH$, $A^2(CH_2)_q$ is $—CH_2C(=O)OH$, r is two, s is three, t is one and u is zero, then R is —OH, $—NH_2$, —NHAc, or

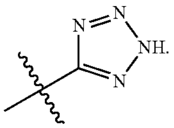

The present disclosure provides a compound of Formula (I), or a pharmaceutically acceptable salt thereof, having one, two, or three or more of the following features:

a) R is $—SO_2CH_3$ or —OH;

b) $A^1$ is $—CO_2H$;

c) $A^2$ is

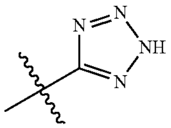 [SMILES: *c1nn[nH]n1]

or $—CO_2H$;

d) p is two;

e) q is one;

f) r is two;

g) s is three;

h) t is one; and i) u is zero, wherein if $A^1(CH_2)_p$ is $—CH_2CH_2C(=O)OH$, $A^2(CH_2)_q$ is $—CH_2C(=O)OH$, r is two, s is three, t is one and u is zero, then R cannot be $SO_2CH_3$. In some embodiments, wherein if $A^1(CH_2)_p$ is $—CH_2CH_2C(=O)OH$, $A^2(CH_2)_q$ is $—CH_2C(=O)OH$, r is two, s is three, t is one and u is zero, then R is —OH, $—NH_2$, —NHAc, or

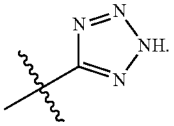 [SMILES: *c1nn[nH]n1]

The present disclosure provides a compound of Formula (I), or a pharmaceutically acceptable salt thereof, having one, two, or three of the following features:

a) R is $—SO_2CH_3$;
b) $A^1$ is $—CO_2H$; and

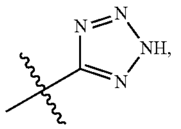 [SMILES: *c1nn[nH]n1]

c) $A^2$ is wherein if $A^1(CH_2)_p$ is $—CH_2CH_2C(═O)OH$, $A^2(CH_2)_q$ is $—CH_2C(═O)OH$, r is two, s is three, t is one and u is zero, then R cannot be $SO_2CH_3$. In some embodiments, wherein if $A^1(CH_2)_p$ is $—CH_2CH_2C(═O)OH$, $A^2(CH_2)_q$ is $—CH_2C(═O)OH$, r is two, s is three, t is one and u is zero, then R is —OH, $—NH_2$, —NHAc, or

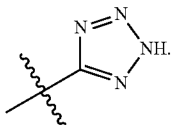 [SMILES: *c1nn[nH]n1]

The present disclosure provides a compound of Formula (I), or a pharmaceutically acceptable salt thereof, having one, two, or three or more of the following features:
a) R is $—SO_2CH_3$;
b) $A^1$ is $—CO_2H$;
c) $A^2$ is

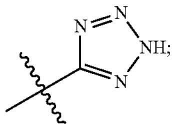 [SMILES: *c1nn[nH]n1]

d) p is two;
e) q is one;
f) r is two;
g) s is three;
h) t is one; and
i) u is zero, wherein if $A^1(CH_2)_p$ is $—CH_2CH_2C(═O)OH$, $A^2(CH_2)_q$ is $—CH_2C(═O)OH$, r is two, s is three, t is one and u is zero, then R cannot be $SO_2CH_3$. In some embodiments, wherein if $A^1(CH_2)_p$ is $—CH_2CH_2C(═O)OH$, $A^2(CH_2)_q$ is $—CH_2C(═O)OH$, r is two, s is three, t is one and u is zero, then R is —OH, $—NH_2$, —NHAc, or

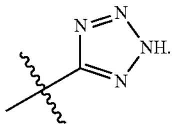 [SMILES: *c1nn[nH]n1]

The present disclosure provides a compound of Formula (I), or a pharmaceutically acceptable salt thereof, having one, two, or three of the following features:
a) R is —OH;
b) $A^1$ is $—CO_2H$; and
c) $A^2$ is $—CO_2H$.

The present disclosure provides a compound of Formula (I), or a pharmaceutically acceptable salt thereof, having one, two, or three or more of the following features:
a) R is —OH;
b) $A^1$ is $—CO_2H$;
c) $A^2$ is $—CO_2H$;
d) p is two;
e) q is one;
r is two;
g) s is three;
h) t is one; and
i) u is zero.

The present disclosure provides a compound of Formula (I), or a pharmaceutically acceptable salt thereof, having one, two, or three of the following features:
a) R is —OH;
b) $A^1$ is $—CO_2H$; and
c) $A^2$ is

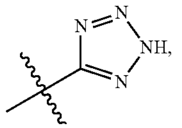 [SMILES: *c1nn[nH]n1]

wherein if $A^1(CH_2)_p$ is $—CH_2CH_2C(═O)OH$, $A^2(CH_2)_q$ is $—CH_2C(═O)OH$, r is two, s is three, t is one and u is zero, then R cannot be $SO_2CH_3$. In some embodiments, wherein if $A^1(CH_2)_p$ is $—CH_2CH_2C(═O)OH$, $A^2(CH_2)_q$ is $—CH_2C(═O)OH$, r is two, s is three, t is one and u is zero, then R is —OH, $—NH_2$, —NHAc, or

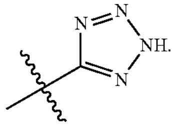 [SMILES: *c1nn[nH]n1]

The present disclosure provides a compound of Formula (I), or a pharmaceutically acceptable salt thereof, having one, two, or three or more of the following features:
a) R is —OH;
b) $A^1$ is $—CO_2H$;
c) $A^2$ is

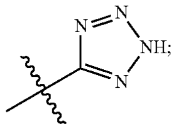 [SMILES: *c1nn[nH]n1]

d) p is two;
e) q is one;
f) r is two;
g) s is three;
h) t is one; and
i) u is zero, wherein if $A^1(CH_2)_p$ is $—CH_2CH_2C(═O)OH$, $A^2(CH_2)_q$ is $—CH_2C(═O)OH$, r is two, s is three, t is one and u is zero, then R cannot be $SO_2CH_3$. In some embodiments, wherein if $A^1(CH_2)_p$ is $—CH_2CH_2C(═O)OH$, $A^2(CH_2)_q$ is $—CH_2C(═O)OH$, r is two, s is three, t is one and u is zero, then R is —OH, $—NH_2$, —NHAc, or

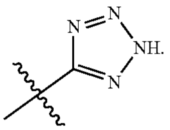 [SMILES: *c1nn[nH]n1]

In certain embodiments, the compound of Formula (I) is a compound of Formula (Ia) or Formula (Ib), (Ia)

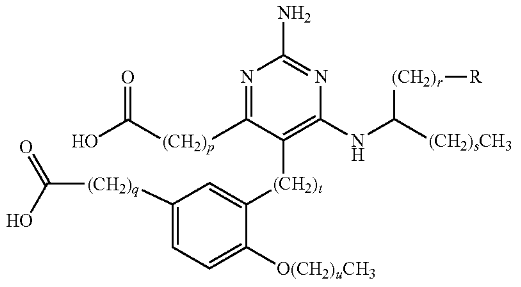

(Ib)

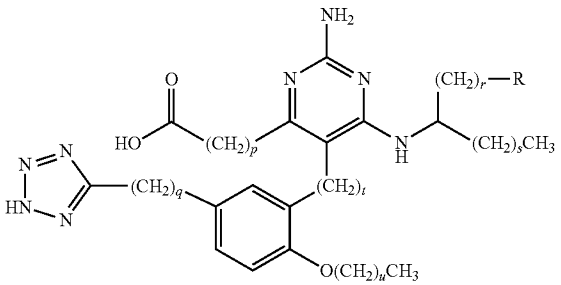

wherein R is selected from the group consisting of —OH, —$SO_2CH_3$, —$NH_2$, —NHAc, and

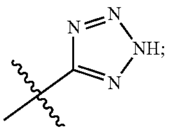 [SMILES: *c1nn[nH]n1]

and p, q, r, s, t, and u are independently selected from zero to four.

In some embodiments, wherein the compound of Formula (I) is a compound of Formula (Ia), and if p is two, q is one, r is two, s is three, t is one and u is zero, then R cannot be $SO_2CH_3$. In some embodiments, wherein the compound of Formula (I) is a compound of Formula (Ia), and if p is two, q is one, r is two, s is three, t is one and u is zero, then R is —OH, —$NH_2$, —NHAc, or

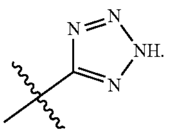 [SMILES: *c1nn[nH]n1]

In certain embodiments, the disclosure provides a compound of Formula (I), or a pharmaceutically acceptable salt thereof, having one, two, or three or more of the following features:

a) R is —$SO_2CH_3$ or —OH;
b) p is two;
c) q is one;
d) r is two;
e) s is three;
f) t is one; and
g) u is zero, wherein if $A^1(CH_2)_p$ is —$CH_2CH_2C$(═O)OH, $A^2(CH_2)_q$ is —$CH_2C$(═O)OH, r is two, s is three, t is one and u is zero, then R cannot be $SO_2CH_3$.

The present disclosure provides a compound of Formula (I), or a pharmaceutically acceptable salt thereof, wherein if $A^1(CH_2)_p$ is —$CH_2CH_2C$(═O)OH, $A^2(CH_2)_q$ is —$CH_2C$(═O)OH, r is two, s is three, t is one and u is zero, then R cannot be $SO_2CH_3$.

In certain embodiments, the disclosure provides a compound of Formula (Ia), Formula (Ib), or a pharmaceutically acceptable salt thereof, having one, two, or three or more of the following features:

a) R is —$SO_2CH_3$ or —OH;
b) p is two;
c) q is one;
d) r is two;
e) s is three;
f) t is one; and
g) u is zero.

In some embodiments, wherein the compound of Formula (I) is a compound of Formula (Ia), wherein if p is two, q is one, r is two, s is three, t is one and u is zero, then R cannot be $SO_2CH_3$. In some embodiments, wherein the compound of Formula (I) is a compound of Formula (Ia), and if p is two, q is one, r is two, s is three, t is one and u is zero, then R is —OH, —$NH_2$, —NHAc, or

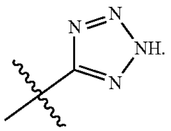 [SMILES: *c1nn[nH]n1]

The present disclosure provides a compound of Formula (I), or a pharmaceutically acceptable salt thereof, having one, two, or three or more of the following features:

a) R is —$SO_2CH_3$;
b) p is two;
c) q is one;
d) r is two;
e) s is three;
f) t is one; and
g) u is zero, wherein if $A^1(CH_2)_p$ is —$CH_2CH_2C$(═O)OH, $A^2(CH_2)_q$ is —$CH_2C$(═O)OH, r is two, s is three, t is one and u is zero, then R cannot be $SO_2CH_3$.

The present disclosure provides a compound of Formula (Ia), Formula (Ib), or a pharmaceutically acceptable salt thereof, having one, two, or three or more of the following features:

a) R is —$SO_2CH_3$;
b) p is two;
c) q is one;
d) r is two;

e) s is three;
f) t is one; and
g) u is zero.

In some embodiments, wherein the compound of Formula (I) is a compound of Formula (Ia), wherein if p is two, q is one, r is two, s is three, t is one and u is zero, then R cannot be $SO_2CH_3$. In some embodiments, wherein the compound of Formula (I) is a compound of Formula (Ia), and if p is two, q is one, r is two, s is three, t is one and u is zero, then R is —OH, —$NH_2$, —NHAc, or

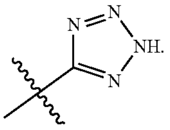 [SMILES: *c1nn[nH]n1]

The present disclosure provides a compound of Formula (Ia), Formula (Ib), or a pharmaceutically acceptable salt thereof, wherein R is —OH.

The present disclosure provides a compound of Formula (Ia), Formula (Ib), or a pharmaceutically acceptable salt thereof, having one, two, or three or more of the following features:

a) R is —OH;
b) p is two;
c) q is one;
d) r is two;
e) s is three;
f) t is one; and
g) u is zero.

In some embodiments, wherein the compound of Formula (I) is a compound of Formula (Ia), and if p is two, q is one, r is two, s is three, t is one and u is zero, then R cannot be $SO_2CH_3$. In some embodiments, wherein the compound of Formula (I) is a compound of Formula (Ia), and if p is two, q is one, r is two, s is three, t is one and u is zero, then R is —OH, —$NH_2$, —NHAc, or

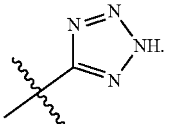 [SMILES: *c1nn[nH]n1]

In certain embodiments, the disclosure provides a compound, or a pharmaceutically acceptable salt thereof, selected from the group consisting of:

| Compound | |
|---|---|
| 1A | 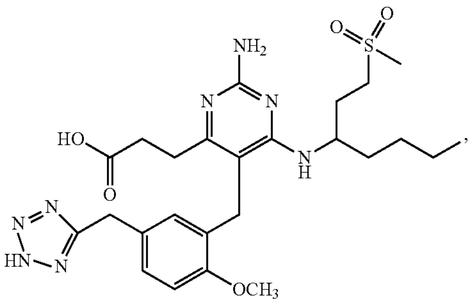 , |

-continued

| Compound | |
|---|---|
| 2A | 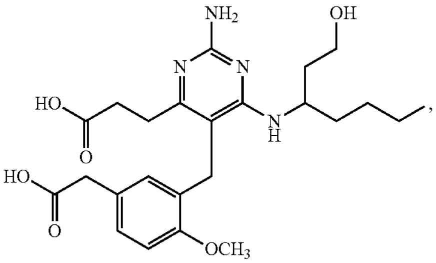 , and |
| 3A | 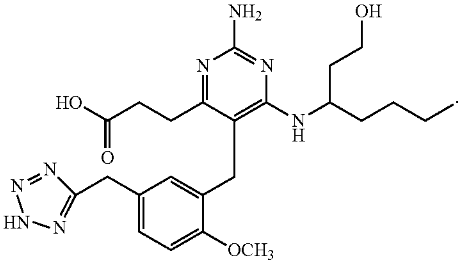 |

In certain embodiments, the disclosure provides a compound, or a pharmaceutically acceptable salt thereof, selected from the group consisting of:

1B

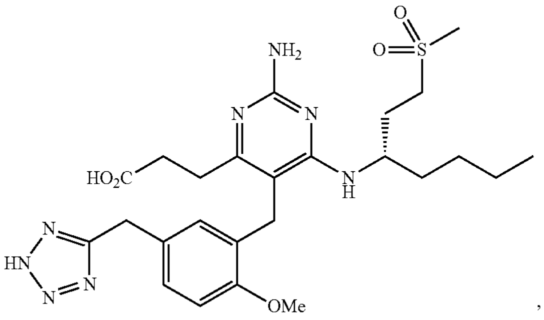

,

2B

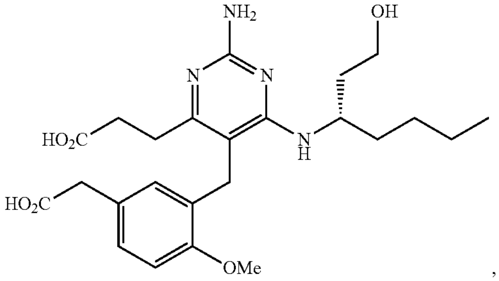

, and

-continued

3B

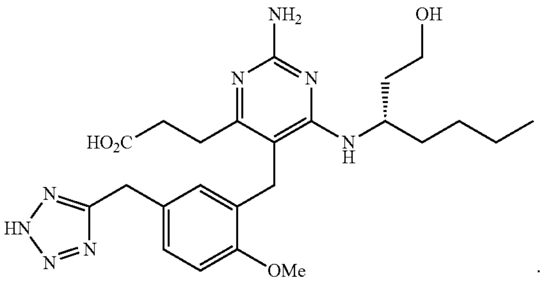

In some embodiments, the compound is Compound 1A or a pharmaceutically acceptable salt thereof. In some embodiments, the compound is Compound 2A or a pharmaceutically acceptable salt thereof. In some embodiments, the compound is Compound 3A or a pharmaceutically acceptable salt thereof. In some embodiments, the compound is Compound 1B or a pharmaceutically acceptable salt thereof. In some embodiments, the compound is Compound 2B or a pharmaceutically acceptable salt thereof. In some embodiments, the compound is Compound 3B or a pharmaceutically acceptable salt thereof.

In certain embodiments, the disclosure provides a compound having the structure of Formula (I), or a pharmaceutically acceptable salt thereof, wherein the compound is a single enantiomer. In certain embodiments, the stereocenter of the carbon bearing $(CH_2)_r$—R, $(CH_2)_sCH_3$ and —NH is the (S)-enantiomer. In certain embodiments, the stereocenter of the carbon bearing $(CH_2)_r$—R, $(CH_2)_sCH_3$ and —NH is the (R)-enantiomer.

Unless otherwise stated, structures depicted herein are also meant to include compounds which differ only in the presence of one or more isotopically enriched atoms. For example, compounds having the present structure except for the replacement of a hydrogen atom by deuterium or tritium, or the replacement of a carbon atom by $^{13}C$ or $^{14}C$, or the replacement of a nitrogen atom by $^{15}N$, or the replacement of an oxygen atom with $^{17}O$ or $^{18}O$ are within the scope of the present disclosure. Such isotopically labeled compounds are useful as research or diagnostic tools.

General Synthetic Methods

As noted herein, the present disclosure includes specific representative compounds, which are identified herein with particularity. The compounds of the present disclosure may be made by a variety of methods, including well-known standard synthetic methods. Illustrative general synthetic methods are set out below and then specific compounds of the present disclosure are prepared in the working Examples.

In all of the examples described below, protecting groups for sensitive or reactive groups are employed where necessary in accordance with general principles of synthetic chemistry. Protecting groups are manipulated according to standard methods of organic synthesis (T. W. Greene and P. G. M. Wuts, *Protecting Groups in Organic Synthesis,* 3$^{rd}$ Edition, John Wiley & Sons, New York (1999)). These groups are removed at a convenient stage of the compound synthesis using methods that are readily apparent to those skilled in the art. The selection of processes as well as the reaction conditions and order of their execution shall be consistent with the preparation of compounds of the present disclosure.

A representative synthesis for compound intermediate and subject compounds is shown in the following Schemes.

Scheme 1: Synthesis of Generic Compound Intermediate

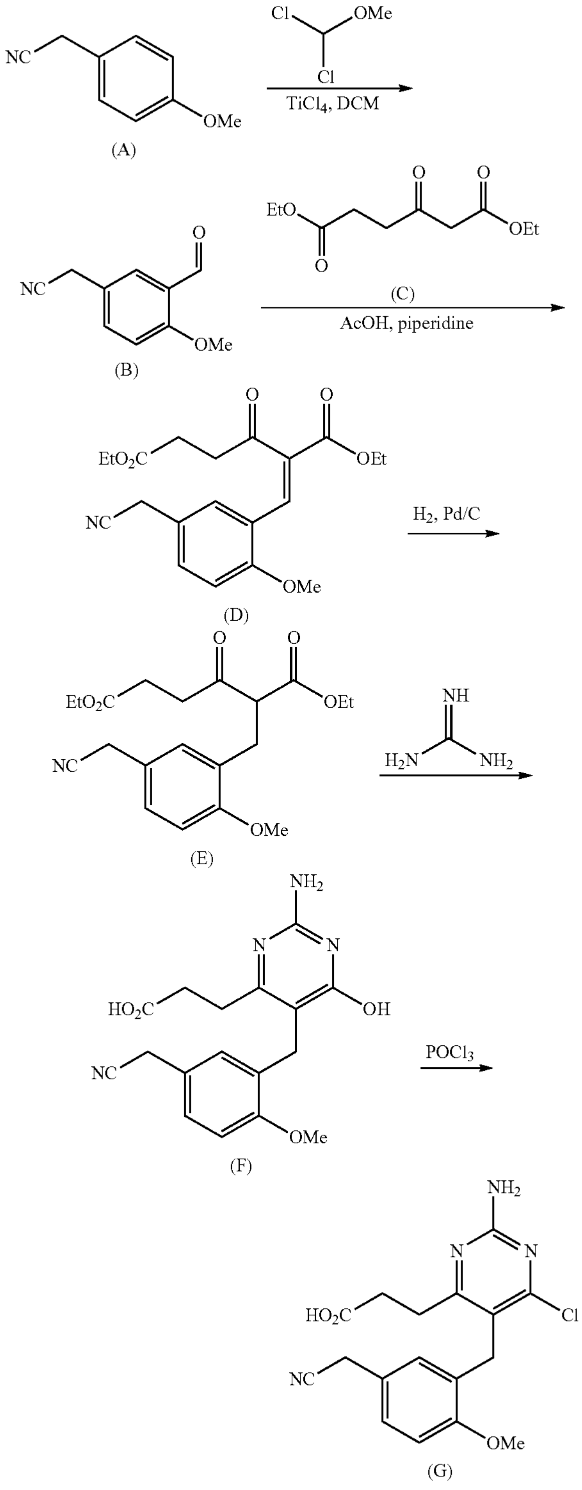

In Scheme 1, compound of Formula (A) can be formylated using a suitable reagent to give Formula (B). Formula (B) can then undergo condensation reaction with formula (C) in presence of acetic acid and piperidine to give Formula (D). Formula (D) can be reduced under standard hydrogenation conditions to afford Formula (E). Formula (E) can react with guanidine carbonate to form the pyrimidine ring as in Formula (F). Formula (F) can be treated with $POCl_3$ to give the corresponding Formula (G), which is used in subsequent transformations to provide the compounds exemplified herein.
Scheme 2: Synthesis of Generic Compounds (K) and (L)
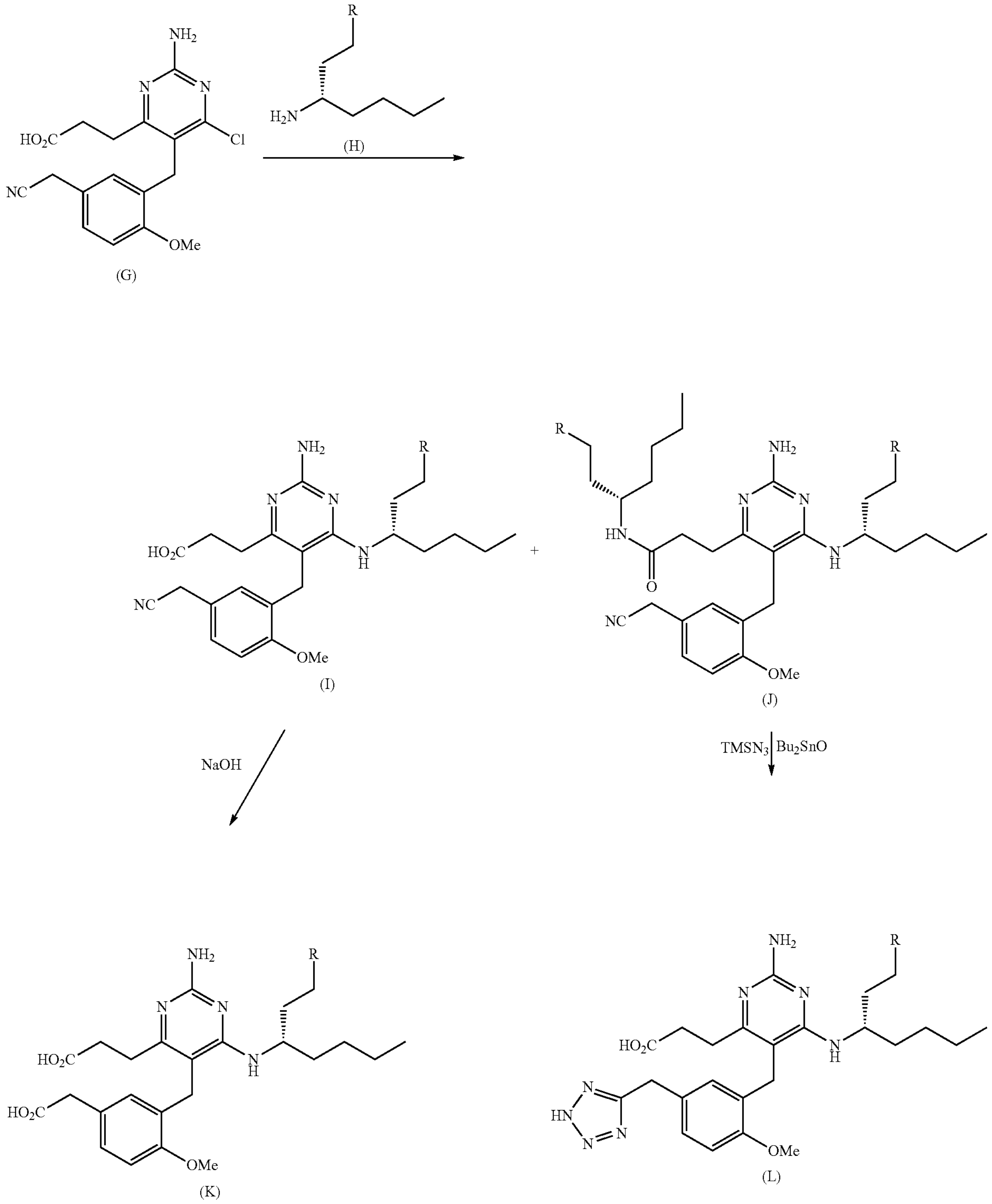

In Scheme 2, compound of Formula (G) can be substituted by an amine with Formula (H) to give a mixture of mono-substituted compound with Formula (I) and di-substituted compound with Formula (J). Compound of Formula (I) can be further hydrolyzed to the carboxylic acid to provide compound of Formula (K). Compound of Formula (J) can be further converted to the tetrazole to provide compound of Formula (L).

A representative synthesis for subject compounds is shown in Scheme 3.

Scheme 3

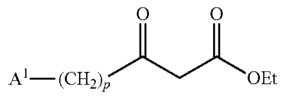

(A')

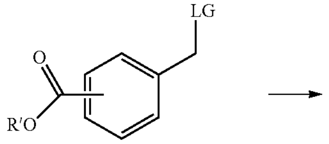

(B')

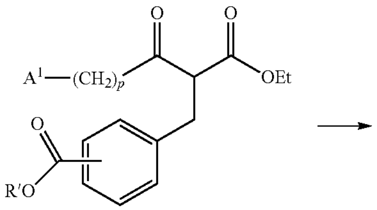

(C')

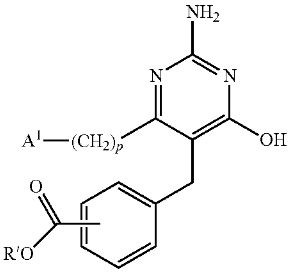

(D')

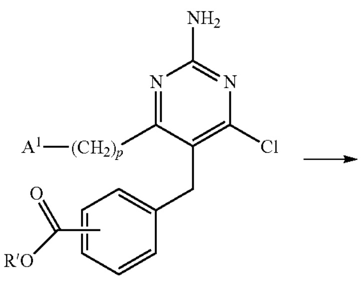

(E')

-continued

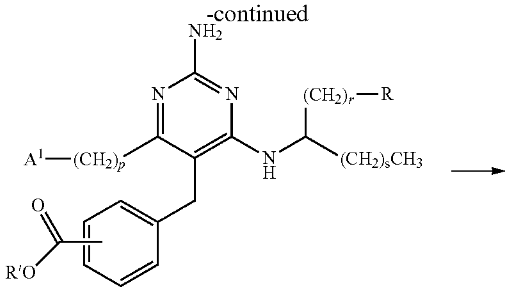

(F')

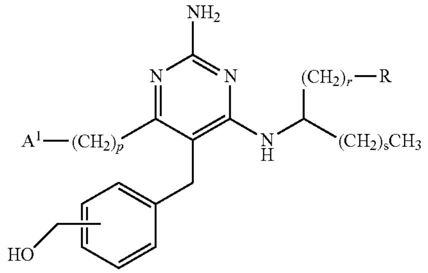

(G')

In Scheme 3, LG is a leaving group; and R' is H or alkyl. Compounds of Formula (A') and (B') are commercially available starting materials. Alternatively, compounds of Formula (A') and (B') can be synthesized via a variety of different synthetic routes using commercially available starting materials and/or starting materials prepared by conventional synthetic methods.

With continued reference to Scheme 3, compounds of Formula (C') may be prepared by reacting a compound of Formula (A') with a base, such as sodium hydride, in a suitable solvent such as tetrahydrofuran or N,N-dimethylformamide at a temperature, for example, from 0° C. to room temperature (20° C.), followed by addition of a compound of formula (B'). The reaction is then preferably heated at a temperature, for example, from 50° C. to 100° C., optionally in the presence of an additive such as potassium iodide.

Compounds of Formula (D') may be prepared by reacting a compound of Formula (C') with guanidine or guanidine carbonate in a suitable solvent such as methanol or ethanol at a temperature, for example, in the range from 50° C. to 150° C.

Compounds of Formula (E') may be prepared by reacting a compound of Formula (D') with phosphorous oxychloride, at a temperature, for example, from 50° C. to 110° C.

Compounds of Formula (F') may be prepared by reacting a compound of formula (E) with excess of an amine of Formula $-NH_2CH(CH_2)_rR(CH_2)_sCH_3$, in a suitable solvent such as NMP, butanol or 1,2-dioxane at a temperature, for example, from 50° C. to 150° C. Alternatively, the reaction can be performed in a microwave at a temperature, for example, from 50° C. to 200° C.

Compounds of Formula (G') may be prepared by reacting a compound of Formula (F') with a reducing agent, such as lithium aluminum hydride, in a suitable solvent such as tetrahydrofuran at a temperature, for example, from 0° C. to 60° C.

A representative synthesis for subject compounds is shown in Scheme 4.

Scheme 4

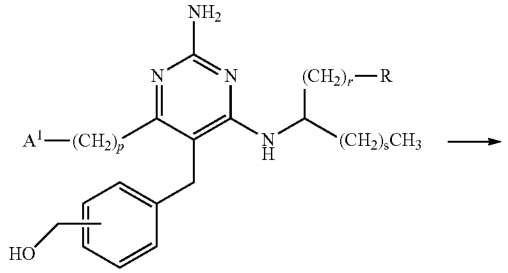

(G')

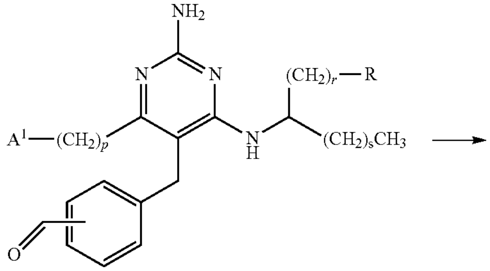

(H')

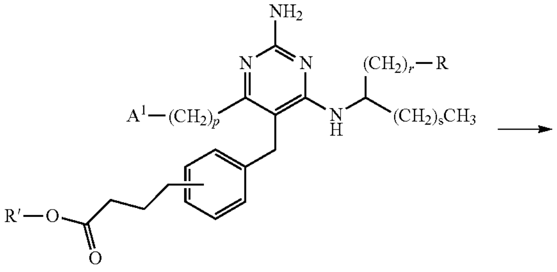

(I')

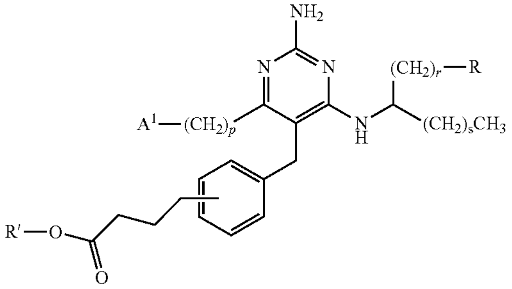

(J')

As illustrated in Scheme 4, compounds of Formula (H') may be prepared by reacting a compound of formula (G') with an oxidizing agent, such as manganese oxide, in a suitable solvent such as tetrahydrofuran or N,N-dimethylformamide at a temperature, for example, from 40° C. to 100° C.

Compounds of Formula (I') may be prepared by reacting a compound of Formula (H') via a Wittig reaction with R'O—C(O)—CH=$PPh_3$. The reaction may be carried out in a suitable solvent, such as tetrahydrofuran, at a temperature, for example, from 50° C. to 150° C. R' is H or alkyl.

Compounds of Formula (J') may be prepared by the reduction of a compound of Formula (I') under hydrogenation conditions. The reaction may be carried out with a catalyst such as palladium on carbon under a hydrogen atmosphere in a suitable solvent such as ethyl acetate at a temperature, for example, from 20° C. to 100° C.

A representative synthesis for subject compounds is shown in Scheme 5.

Scheme 5

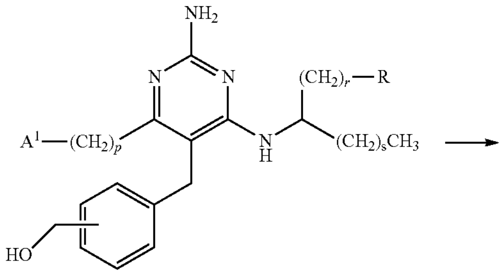

(G')

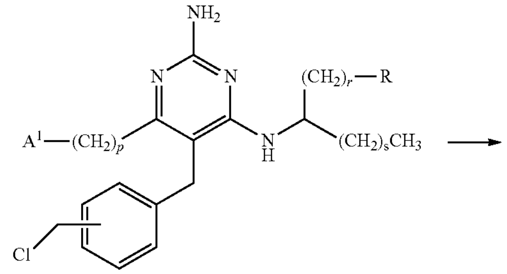

(K')

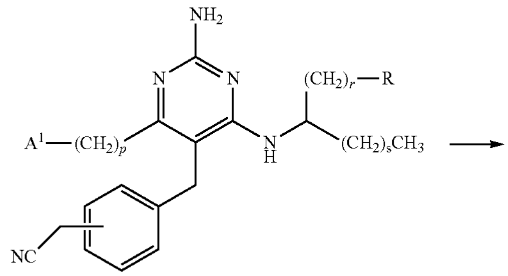

(L')

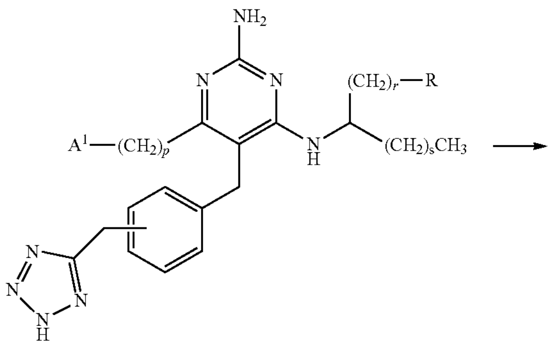

(M')

-continued

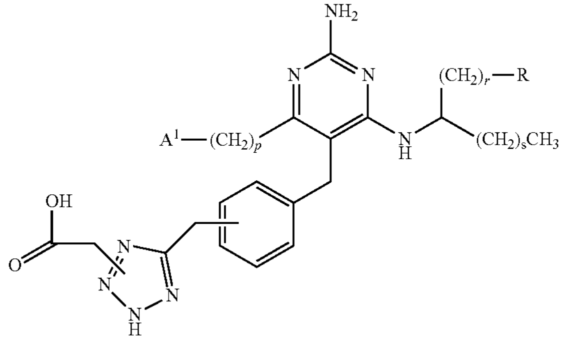

(N')

As illustrated in Scheme 5, compounds of Formula (K') may be prepared by reacting a compound of Formula (G') with a chlorinating reagent, such as thionyl chloride in a suitable solvent such as methylene chloride at a temperature, for example, from room temperature to 50° C.

Compounds of Formula (L') may be prepared by reacting a compound of Formula (K') with a cyanide salt, such as potassium cyanide, in a suitable solvent such as dimethylsulfoxide or N,N-dimethylformamide (or a mixture of both solvents) at a temperature, for example, from room temperature to 50° C.

Compounds of formula (M') may be prepared by reacting a compound of Formula (L') with an azido reagent, such as trimethylsilyl azide, in an azide-nitrile cycloaddition. The reaction can be run in a suitable solvent such as NMP or dioxane at a temperature, for example, from 50° C. to 150° C. The reaction may be done in the presence of catalyst, such as dibutyltin oxide.

Compounds of Formula (N') may be prepared by reacting a compound of Formula (M') with an alkylating agent, such as 2-bromoacetate, in a suitable solvent such as acetone at a temperature, for example, from 0° C. to 60° C.

A representative synthesis for subject compounds is shown in Scheme 6.

Scheme 6

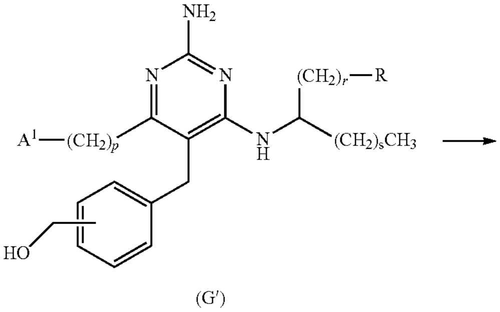

(G')

-continued

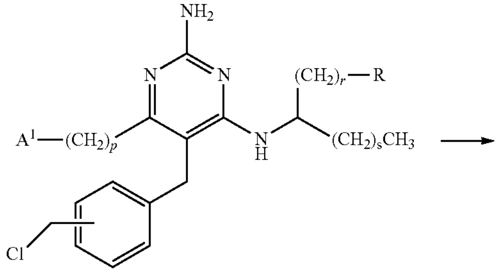

(K')

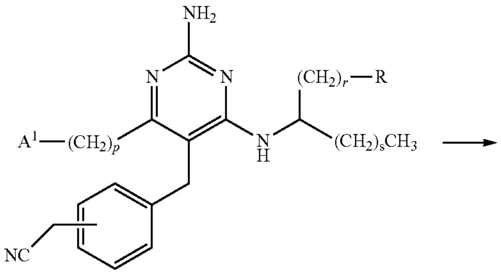

(L')

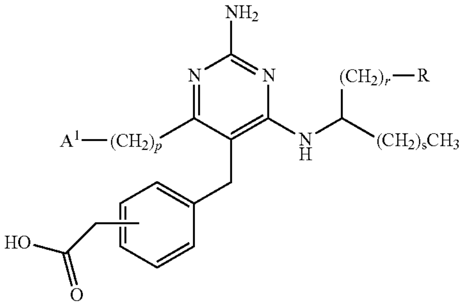

(O')

Preparation of compounds of Formula (K') and (L') are described above in Scheme 5. As illustrated in Scheme 6, compounds of Formula (O') may be prepared by hydrolyzing a compound of Formula (L'), such as with use of a base, such as potassium hydroxide, in a suitable solvent such as ethane-1,2-diol and water (or mixtures thereof) at a temperature, for example, from 50° C. to 200° C.

A representative synthesis for subject compounds is shown in Scheme 7.

Scheme 7

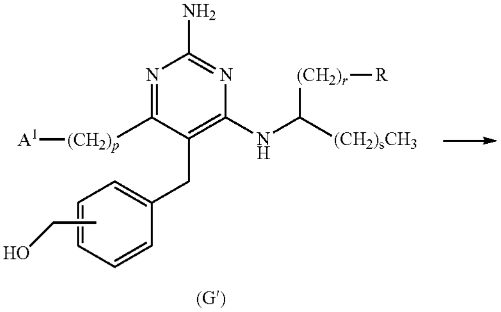

(G')

-continued

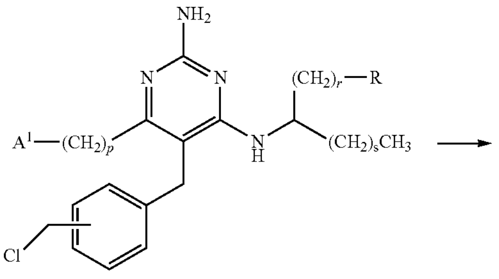

(K')

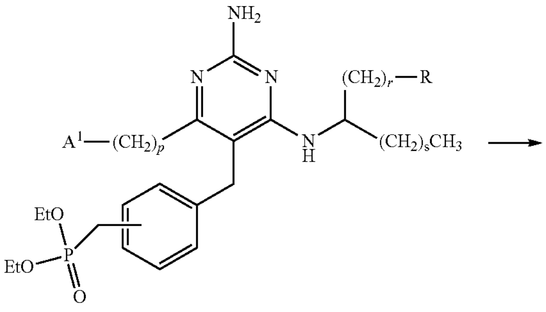

(P')

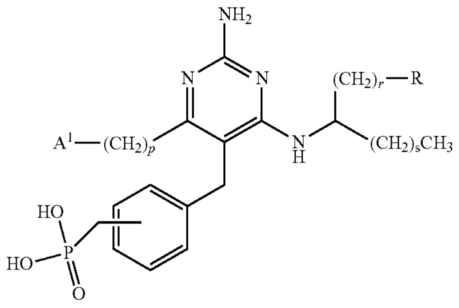

(Q')

Preparation of compound of Formula (K') is described above in Scheme 5. As illustrated in Scheme 7, compounds of Formula (P') may be prepared by reacting a compound of Formula (K') with triethylphosphite, in a suitable solvent or neatly at a temperature, for example, from 50° C. to 150° C.

Compounds of Formula (Q') may be prepared by reacting a compound of Formula (P') with reagents to remove the ethyl groups, such as bromotrimethylsilane, in a suitable solvent such as methylene chloride at a temperature, for example, from room temperature to 60° C.

A representative synthesis for subject compounds is shown in Scheme 8.

Scheme 8

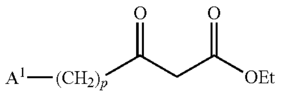

(A')

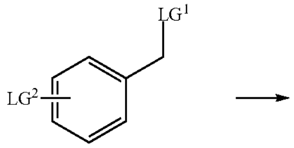

(B")

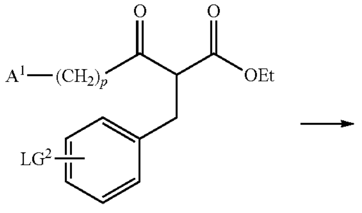

(C")

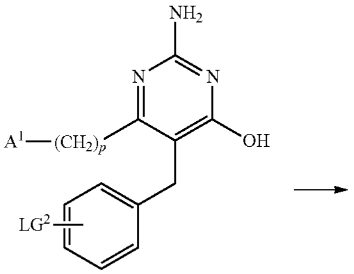

(D")

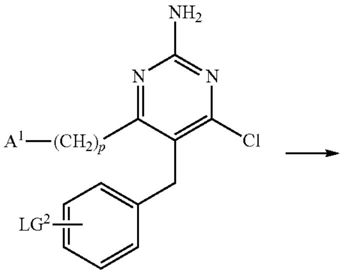

(E")

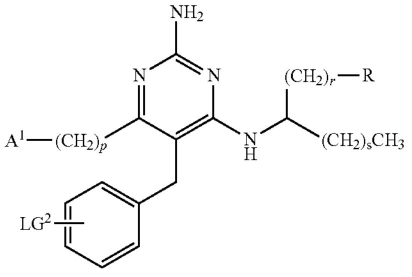

(F")

In Scheme 8, $LG^1$ and $LG^2$ are leaving groups. Compounds of Formula (A') and (B") are commercially available starting materials. Alternatively, compounds of Formula (A') and (B") can be synthesized via a variety of different synthetic routes using commercially available starting materials and/or starting materials prepared by conventional synthetic methods.

As illustrated in Scheme 8, compounds of Formula (C") may be prepared by reacting a compound of Formula (A') with a base, such as sodium hydride, in a suitable solvent such as tetrahydrofuran or N,N-dimethylformamide at a temperature, for example, from 0° C. to room temperature (20° C.), followed by addition of a compound of Formula (B"). The reaction is then preferably heated at a temperature, for example, from 50° C. to 100° C., optionally in the presence of an additive such as potassium iodide.

Compounds of Formula (D") may be prepared by reacting a compound of Formula (C") with guanidine or guanidine carbonate in a suitable solvent such as methanol or ethanol at a temperature, for example, in the range from 50° C. to 150° C.

Compounds of Formula (E") may be prepared by reacting a compound of Formula (D") with phosphorous oxychloride, at a temperature, for example, from 50° C. to 110° C.

Compounds of Formula (F") may be prepared by reacting a compound of Formula (E") with excess of an amine of formula $NH_2CH(CH_2)_rR(CH_2)_sCH_3$, in a suitable solvent such as NMP, butanol or 1,2-dioxane at a temperature, for example, from 50° C. to 150° C. Alternatively, the reaction can be performed in a microwave at a temperature, for example, from 50° C. to 200° C.

A representative synthesis for subject compounds is shown in Scheme 9.

Scheme 9

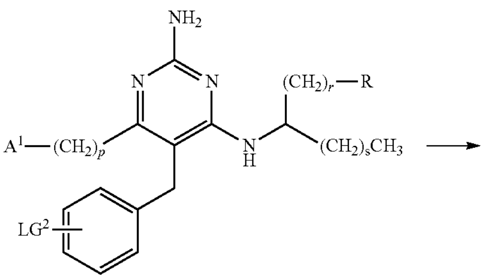

(F")

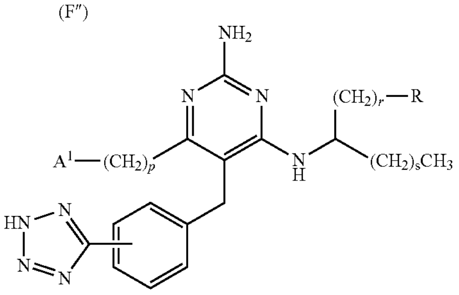

(G")

As illustrated in Scheme 9, compounds of Formula (G") may be prepared by reacting a compound of Formula (F") with an azido reagent, such as trimethylsilyl azide, in an azide-nitrile cycloaddition. $LG^2$ is a leaving group. The reaction can be run in a suitable solvent such as NMP or dioxane at a temperature, for example, from 50° C. to 150° C. The reaction may be done in the presence of catalyst, such as dibutyltin oxide.

A representative synthesis for subject compounds is shown in Scheme 10.

Scheme 10

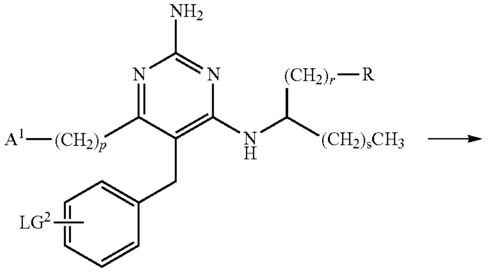

(F")

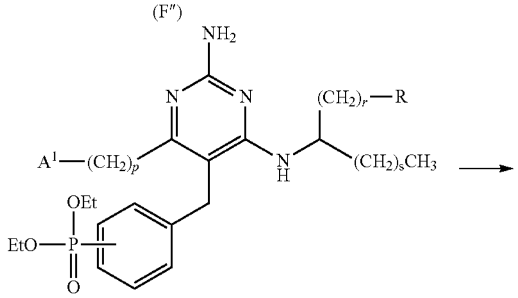

(I")

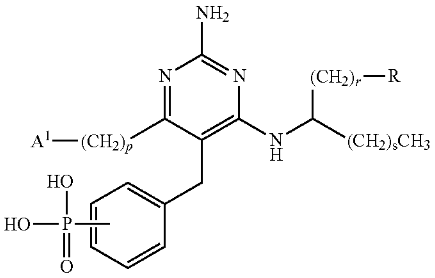

(J")

As illustrated in Scheme 10, compounds of Formula (I") may be prepared by reacting a compound of Formula (F") with triethylphosphite, in a suitable solvent or neatly at a temperature, for example, from 50° C. to 150° C. $LG^2$ is a leaving group.

Compounds of Formula (J") may be prepared by reacting a compound of Formula (I") with reagents to remove the ethyl groups, such as bromotrimethylsilane, in a suitable solvent such as methylene chloride at a temperature, for example, from room temperature to 60° C.

Method of Treatment

The compounds of Formula I, Ia, Ib, 1A-3A, and 1B-3B, and their pharmaceutically acceptable salts have activity as pharmaceuticals, in particular as modulators of toll-like receptor (especially TLR7) activity.

The present disclosure provides a method of treating a respiratory condition comprising administering to a subject in need thereof an effective amount of a compound of the present disclosure, or a pharmaceutically acceptable salt thereof. In one embodiment, the respiratory condition is a lung cancer.

The present disclosure provides a method of treating a respiratory condition comprising administering to a subject in need thereof an effective amount of a pharmaceutical composition of the present disclosure. In one embodiment, the respiratory condition is a lung cancer.

Compounds of Formula I, Ia, Ib, 1A-3A, and 1B-3B, and their pharmaceutically acceptable salts may be used in the treatment of a respiratory condition, which includes conditions related to the respiratory tract. Respiratory condition as used herein, also includes cancers. The following are non-limiting examples of respiratory conditions contemplated by this disclosure:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all seventies, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus; and
2. oncology: treatment of common cancers including a cancer of the upper and lower airway, lung, gastrointestinal (including esophageal), head and neck, and ear/nose/throat; including the prevention and treatment of metastatic disease and tumor recurrences.

In particular, compounds of Formula I, Ia, Ib, 1A-3A, and 1B-3B, and their pharmaceutically acceptable salts may be used in the treatment of a respiratory disease. In some embodiments, the respiratory condition is a cancer. In particular, embodiments, the cancer is selected from lung cancer, a cancer of the upper and lower airway, a head and neck cancer, and an ear/nose/throat cancer. In one embodiment, the respiratory condition is lung cancer. In alternative embodiments, the respiratory condition is non-cancerous. In particular embodiments the non-cancerous respiratory condition is selected from the group consisting of asthma, allergy, and chronic obstructive pulmonary disease (COPD).

In some embodiments, compounds of Formula I, Ia, Ib, 1A-3A, and 1B-3B, and their pharmaceutically acceptable salts may be used to treat a respiratory condition related to an aerodigestive condition. An aerodigestive condition may be a condition related to the organs and tissues of the respiratory tract and upper part of the digestive tract including the lips, mouth, tongue, nose, throat, vocal cords, and part of the esophagus and windpipe. In certain embodiments the aerodigestive condition is cancer of the ear, nose, or throat.

In one aspect, the present disclosure provides the use of a compound of Formula I, Ia, Ib, 1A-3A, or 1B-3B, or a pharmaceutically acceptable salt thereof, as an adjuvant. In another aspect, the present disclosure provides the use of a compound of Formula I, Ia, Ib, 1A-3A, or 1B-3B, or a pharmaceutically acceptable salt thereof, to treat cancer. In yet another aspect, the present disclosure provides the use of a compound of Formula I, Ia, Ib, 1A-3A, or 1B-3B, or a pharmaceutically acceptable salt thereof, to treat cancer and as an adjuvant. In yet another aspect, the present disclosure provides the use of a compound of Formula I, Ia, Ib, 1A-3A, or 1B-3B, or a pharmaceutically acceptable salt thereof, to treat cancer and/or as an adjuvant.

In another aspect, the present disclosure provides the use of a compound of Formula I, Ia, Ib, 1A-3A, or 1B-3B, or a pharmaceutically acceptable salt thereof, to treat a respiratory disease. In yet another aspect, the present disclosure provides the use of a compound of Formula I, Ia, Ib, 1A-3A, or 1B-3B, or a pharmaceutically acceptable salt thereof, to treat a respiratory condition and as an adjuvant. In yet another aspect, the present disclosure provides the use of a compound of Formula I, Ia, Ib, 1A-3A, or 1B-3B, or a pharmaceutically acceptable salt thereof, to treat a respiratory condition and/or as an adjuvant. In some embodiments, the respiratory condition is cancer. In more specific embodiments, the respiratory condition is lung cancer.

Thus, the present disclosure provides a compound of Formula I, Ia, Ib, 1A-3A, or 1B -3B, or a pharmaceutically-acceptable salt thereof as hereinbefore defined for use in therapy.

In a further aspect, the present disclosure provides the use of a compound of Formula I, Ia, Ib, 1A-3A, or 1B-3B, or a pharmaceutically acceptable salt thereof as hereinbefore defined in the manufacture of a medicament for use in therapy. In particular embodiments, the medicament is used to treat a respiratory disease.

The present disclosure provides a method of treating a respiratory condition associated with TLR7 modulation in a subject in need thereof, comprising administering to the subject an effective amount of a compound of the present disclosure, or a pharmaceutically acceptable salt thereof. The present disclosure also provides a compound of the present disclosure, or a pharmaceutically acceptable salt thereof, for use in treating a condition associated with TLR7 modulation. The present disclosure provides use of a compound of the present disclosure, or a pharmaceutically acceptable salt thereof, in the manufacture of a medicament for treating a condition associated with TLR7 modulation. In certain embodiments, the respiratory condition is a cancer. In particular, embodiments, the cancer is selected from lung cancer, a cancer of the upper and lower airway, a head and neck cancer, and an ear/nose/throat cancer. In other embodiments the respiratory condition is non-cancerous. In particular embodiments the non-cancerous respiratory condition is selected from the group consisting of asthma, allergy, and chronic obstructive pulmonary disease (COPD).

In some embodiments of the methods described herein, the compound, or pharmaceutically acceptable salt thereof, is administered to the subject in need thereof via inhalation.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

The present disclosure still further provides a method of treating, or reducing the risk of, a disease or condition comprising or arising from abnormal cell growth (e.g. a cancer), which method comprises administering to a patient in need thereof a therapeutically effective amount of a compound of Formula I, Ia, Ib, 1A-3A, or 1B-3B, or a pharmaceutically acceptable salt thereof as hereinbefore defined.

The present disclosure also provides a method of treating, or reducing the risk of, an obstructive airways disease or condition (e.g. asthma or COPD) which comprises administering to a patient in need thereof a therapeutically effective amount of a compound of Formula I, Ia, Ib, 1A-3A, or 1B-3B, or a pharmaceutically acceptable salt thereof as hereinbefore defined.

For the above-mentioned therapeutic uses the dosage administered will, of course, vary with the compound employed, the mode of administration, the treatment desired and the disorder indicated. For example, the daily dosage of the compound of the present disclosure, if inhaled, may be in the range from about 0.05 micrograms per kilogram body weight (μg/kg) to about 100 micrograms per kilogram body weight (μg/kg). Alternatively, if the compound is administered orally, then the daily dosage of the compound of the present disclosure may be in the range from about 0.01 micrograms per kilogram body weight (μg/kg) to about 100 milligrams per kilogram body weight (mg/kg).

Pharmaceutical Compositions

The compounds of Formula I, Ia, Ib, 1A-3A, and 1B-3B, and pharmaceutically acceptable salts thereof may be used on their own but will generally be administered in the form of a pharmaceutical composition in which the Formula I, Ia, Ib, 1A-3A, or 1B-3B, compound/salt (active ingredient) is in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

The present disclosure provides pharmaceutical compositions comprising a compound of the present disclosure, or a pharmaceutically acceptable salt thereof, and a pharmaceutically acceptable carrier. In one embodiment, the pharmaceutically acceptable carrier is carboxy methylcellulose, saline, water, or another aqueous solution. In another embodiment, the pharmaceutically acceptable carrier is 0.1%-5% carboxy methylcellulose in water.

In certain embodiments, the administration can be intranasal, inhaled, or intratracheal.

Depending on the mode of administration, the pharmaceutical composition will comprise from about 0.05 to about 99% w (percent by weight), more particularly from about 0.05 to about 80% w, still more particularly from about 0.10 to about 70% w, and even more particularly from about 0.10 to about 50% w, of active ingredient, all percentages by weight being based on total composition.

The present disclosure also provides a pharmaceutical composition comprising a compound of Formula I, Ia, Ib, 1A-3A, or 1B-3B, or a pharmaceutically acceptable salt thereof as hereinbefore defined, in association with a pharmaceutically acceptable adjuvant, diluent or carrier.

The present disclosure further provides a process for the preparation of a pharmaceutical composition of the present disclosure which comprises mixing a compound of Formula I, Ia, Ib, 1A-3A, or 1B-3B, or a pharmaceutically acceptable salt thereof as hereinbefore defined with a pharmaceutically acceptable adjuvant, diluent or carrier.

The pharmaceutical compositions may be administered topically (e.g. to the skin or to the lung and/or airways) in the form, e.g., of creams, solutions, suspensions, heptafluoroalkane (HFA) aerosols and dry powder formulations, for example, formulations in the inhaler device known as the Turbuhaler®; or systemically, e.g. by oral administration in the form of tablets, capsules, syrups, powders or granules; or by parenteral administration in the form of a sterile solution, suspension or emulsion for injection (including intravenous, subcutaneous, intramuscular, intravascular or infusion); or by rectal administration in the form of suppositories.

Dry powder formulations and pressurized HFA aerosols of the compounds of the present disclosure (including pharmaceutically acceptable salts) may be administered by oral or nasal inhalation. For inhalation, the compound is desirably finely divided. The finely divided compound preferably has a mass median diameter of less than 10 micrometres (μm), and may be suspended in a propellant mixture with the assistance of a dispersant, such as a $C_8$-$C_{20}$ fatty acid or salt thereof, (for example, oleic acid), a bile salt, a phospholipid, an alkyl saccharide, a perfluorinated or polyethoxylated surfactant, or other pharmaceutically acceptable dispersant.

The compounds of the present disclosure may also be administered by means of a dry powder inhaler. The inhaler may be a single or a multi dose inhaler, and may be a breath actuated dry powder inhaler.

One possibility is to mix the finely divided compound of the present disclosure with a carrier substance, for example, a mono-, di- or polysaccharide, a sugar alcohol, or another polyol. Suitable carriers are sugars, for example, lactose, glucose, raffinose, melezitose, lactitol, maltitol, trehalose, sucrose, mannitol; and starch. Alternatively the finely divided compound may be coated by another substance. The powder mixture may also be dispensed into hard gelatin capsules, each containing the desired dose of the active compound.

Another possibility is to process the finely divided powder into spheres which break up during the inhalation procedure. This spheronized powder may be filled into the drug reservoir of a multidose inhaler, for example, that known as the Turbuhaler® in which a dosing unit meters the desired dose which is then inhaled by the patient. With this system the active ingredient, with or without a carrier substance, is delivered to the patient.

Combination Therapy

The compounds of the present disclosure (that is, compounds of Formula I, Ia, Ib, 1A -3A, and 1B-3B, and pharmaceutically acceptable salts thereof) may also be administered in conjunction with other compounds used for the treatment of the above conditions.

The present disclosure therefore further relates to combination therapies wherein a compound of the present disclosure or a pharmaceutical composition or formulation comprising a compound of the present disclosure is administered concurrently or sequentially or as a combined preparation with another therapeutic agent or agents, for the treatment of one or more of the conditions listed.

The anti-cancer treatment defined hereinbefore may be applied as a sole therapy or may involve, in addition to the compound of the present disclosure, conventional surgery or radiotherapy or chemotherapy. Such chemotherapy may include one or more of the following categories of anti-tumour agents:

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341) and N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem. 2004, 47, 6658-6661), and metalloproteinase inhibitors like marimastat, inhibitors of urokinase plasminogen activator receptor function or antibodies to Heparanase);

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stern et al. Critical reviews in oncology/haematology, 2005, Vol. 54, ppl 1-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD 1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib, inhibitors of the hepatocyte growth factor family, inhibitors of the platelet-derived growth factor family such as imatinib, inhibitors of serine/threonine kinases (for example Ras/Raf signaling inhibitors such as farnesyl transferase inhibitors, for example sorafenib (BAY 43-9006)), inhibitors of cell signaling through MEK and/or AKT kinases, inhibitors of the hepatocyte growth factor family, c-kit inhibitors, abl kinase inhibitors, IGF receptor (insulin-like growth factor) kinase inhibitors; aurora kinase inhibitors (for example AZDl 152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and VEGF receptor tyrosine kinase inhibitors such as 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-ylpropoxy)quinazoline (AZD2171; Example 240 within WO 00/47212), vatalanib (PTK787; WO 98/35985) and SUl 1248 (sunitinib; WO 01/60814), compounds such as those disclosed in International Patent Applications WO97/22596, WO 97/30035, WO 97/32856 and WO 98/13354 and compounds that work by other mechanisms (for example linomide, inhibitors of integrin αvβ3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy;

(ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies;

(x) Checkpoint inhibitors, including but not limited to antibodies to PD-1/PD-L1, CTLA -4, TIM-3, LAG-3, OX-40, GITR, VISTA, 4-1BB, CD40, TIGIT, BTLA;

(xi) Kinase inhibitors, including but not limited to small molecule or monoclonal antibody inhibitors of BRAF, EGFR, ALK, RAS, RAF, VEGF, HER, c-MET, MEK, FGFR, BCR-ABL, PI3K;

(xii) Inhibitors of cancer/immune metabolism, including but not limited to inhibitors of IDO, TDO, GLS, IDH, arginase, adenosine receptor, CD73, CD39;

(xiii) Epigenetic modulators, including but not limited to inhibitors of HDAC, bromodomain, methyl transferase;

(xiv) Developmental pathway modulator, including but not limited to Smo, Wnt, YAP;

(xv) Other anti-cancer or immune-oncology biologics including but not limited to oncolytic virus, BCG, CART, cytokines; and (xv) Antibodies including but not limited to PD-1 antibody and PD-L1 antibody.

Furthermore, for the treatment of the inflammatory diseases, COPD, asthma and allergic rhinitis the compounds of the present disclosure may be combined with agents such as tumour necrosis factor alpha (TNF-alpha) inhibitors such as anti-TNF monoclonal antibodies (for example Remicade, CDP-870 and adalimumab) and TNF receptor immunoglobulin molecules (such as Enbrel); non-selective cyclooxygenase COX-1/COX-2 inhibitors whether applied topically or systemically (such as piroxicam, diclofenac, propionic acids such as naproxen, flubiprofen, fenoprofen, ketoprofen and ibuprofen, fenamates such as mefenamic acid, indomethacin, sulindac, azapropazone, pyrazolones such as phenylbutazone, salicylates such as aspirin), COX-2 inhibitors (such as meloxicam, celecoxib, rofecoxib, valdecoxib, lumarocoxib, parecoxib and etoricoxib); corticosteroids; glucocorticosteroids (whether administered by topical, oral, intramuscular, intravenous, or intra-articular routes); beta agonists; anti-histamines; methotrexate, lefunomide; hydroxychloroquine, d-penicillamine, auranofin or other parenteral or oral gold preparations.

The present disclosure still further relates to other innate immune agonists targeting the following classes of receptors, including, but not limited to, TLRs (Toll-like receptor); NLRs (Nod-like receptor); CLRs (C-type lectin receptor); RLRs (RIG-I like receptor); and STING (stimulator of interferon gene).

The present disclosure still further relates to the combination of a compound of the present disclosure and a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; an N-(5-substituted)-thiophene-2-alkylsulfonamide; 2,6-di-tert-butylphenolhydrazones; a methoxytetrahydropyrans such as Zeneca ZD-2138; the compound SB-210661; a pyridinyl-substituted 2-cyanonaphthalene compound such as L -739,010; a 2-cyanoquinoline compound such as L-746,530; or an indole or quinoline compound such as MK-591, MK-886, and BAY x 1005.

The present disclosure further relates to the combination of a compound of the present disclosure and a receptor antagonist for leukotrienes (LTB4, LTC4, LTD4, and LTE4) selected from the group consisting of the phenothiazin-3-ones such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY x 7195.

The present disclosure still further relates to the combination of a compound of the present disclosure and a phosphodiesterase (PDE) inhibitor such as a methylxanthanine including theophylline and aminophylline; a selective PDE isoenzyme inhibitor including a PDE4 inhibitor an inhibitor of the isoform PDE4D, or an inhibitor of PDE5.

The present disclosure further relates to the combination of a compound of the present disclosure and a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine; applied orally, topically or parenterally.

The present disclosure still further relates to the combination of a compound of the present disclosure and a gastroprotective histamine type 2 receptor antagonist.

The present disclosure further relates to the combination of a compound of the present disclosure and an antagonist of the histamine type 4 receptor.

The present disclosure still further relates to the combination of a compound of the present disclosure and an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethylnorepinephrine hydrochloride.

The present disclosure further relates to the combination of a compound of the present disclosure and an anticholinergic agent including muscarinic receptor (M1, M2, and M3) antagonists such as atropine, hyoscine, glycopyrrrolate, ipratropium bromide, tiotropium bromide, oxitropium bromide, pirenzepine or telenzepine.

The present disclosure still further relates to the combination of a compound of the present disclosure together with a beta-adrenoceptor agonist (including beta receptor subtypes 1-4) such as isoprenaline, salbutamol, formoterol, salmeterol, terbutaline, orciprenaline, bitolterol mesylate, and pirbuterol.

The present disclosure further relates to the combination of a compound of the present disclosure and a chromone, such as sodium cromoglycate or nedocromil sodium.

The present disclosure still further relates to the combination of a compound of the present disclosure together with an insulin-like growth factor type I (IGF-I) mimetic.

The present disclosure still further relates to the combination of a compound of the present disclosure and a glucocorticoid, such as flunisolide, triamcinolone acetonide, beclomethasone dipropionate, budesonide, fluticasone propionate, ciclesonide or mometasone furoate.

The present disclosure still further relates to the combination of a compound of the present disclosure together with an inhibitor of matrix metalloproteases (MMPs), i.e., the stromelysins, the collagenases, and the gelatinases, as well as aggrecanase; especially collagenase-1 (MMP-I), collagenase-2 (MMP-8), collagenase-3 (MMP-13), stromelysin-1 (MMP-3), stromelysin-2 (MMP-IO), and stromelysin-3 (MMP-11) and MMP-9 and MMP-12.

The present disclosure still further relates to the combination of a compound of the present disclosure together with modulators of chemokine receptor function such as antagonists of CCR1, CCR2, CCR2A, CCR2B, CCR3, CCR4, CCR5, CCR6, CCR7, CCR8, CCR9, CCR10 and CCR11 (for the C-C family); CXCR1, CXCR2, CXCR3, CXCR4 and CXCR5 (for the C—X—C family) and CX3CR1 for the C-X3-C family.

The present disclosure still further relates to the combination of a compound of the present disclosure together with a cytokine or modulator of cytokine function, including alpha-, beta-, and gamma-interferon; interleukins (IL) including IL1 to 15, and interleukin antagonists or inhibitors, including agents which act on cytokine signaling pathways.

The present disclosure still further relates to the combination of a compound of the present disclosure together with an immunoglobulin (Ig) or Ig preparation or an antagonist or antibody modulating Ig function such as anti-IgE (omalizumab).

The present disclosure further relates to the combination of a compound of the present disclosure and another systemic or topically-applied anti-inflammatory agent, such as thalidomide or a derivative thereof, a retinoid, dithranol or calcipotriol.

The present disclosure further relates to the combination of a compound of the present disclosure together with an antibacterial agent such as a penicillin derivative, a tetracycline, a macrolide, a beta-lactam, a fluoroquinolone, metronidazole, an inhaled aminoglycoside; an antiviral agent including acyclovir, famciclovir, valaciclovir, ganciclovir, cidofovir, amantadine, rimantadine, ribavirin, zanamavir and oseltamavir; a protease inhibitor such as indinavir, nelfinavir, ritonavir, and saquinavir; a nucleoside reverse transcriptase inhibitor such as didanosine, lamivudine, stavudine, zalcitabine or zidovudine; or a non-nucleoside reverse transcriptase inhibitor such as nevirapine or efavirenz.

In a further aspect the present disclosure provides a combination (for example for the treatment of COPD, asthma or allergic rhinitis) of a compound of Formula (I) or a pharmaceutically acceptable salt thereof as hereinbefore defined and one or more agents independently selected from:
- a non-steroidal glucocorticoid receptor (GR-receptor) agonist;
- a selective β2 adrenoceptor agonist (such as metaproterenol, isoproterenol, isoprenaline, albuterol, salbutamol, formoterol, salmeterol, terbutaline, orciprenaline, bitolterol mesylate, pirbuterol or indacaterol);
- a phosphodiesterase inhibitor (such as a PDE4 inhibitor);
- a protease inhibitor (such as a neutrophil elastase or matrix metalloprotease MMP-12 inhibitor);
- a glucocorticoid;
- an anticholinergic agent;
- a modulator of chemokine receptor function (such as a CCR1 receptor antagonist); and
- an inhibitor of kinase function (such as the kinases p38 or IKK).

The present disclosure also provides a pharmaceutical product comprising, in combination, a preparation of a first active ingredient which is a compound of Formula I, Ia, Ib, 1A-3A, or 1B-3B, or a pharmaceutically acceptable salt thereof as hereinbefore defined, and a preparation of a second active ingredient which is
- a non-steroidal glucocorticoid receptor (GR-receptor) agonist;
- a selective β2 adrenoceptor agonist;
- a phosphodiesterase inhibitor;
- a protease inhibitor;
- a glucocorticoid;
- an anticholinergic agent;
- a modulator of chemokine receptor function; or
- an inhibitor of kinase function;

for simultaneous, sequential or separate use in therapy.

In another aspect, the present disclosure provides a kit comprising a preparation of a first active ingredient which is a compound of Formula I, Ia, Ib, 1A-3A, or 1B-3B, or a pharmaceutically acceptable salt thereof as hereinbefore defined, and a preparation of a second active ingredient which is
- a non-steroidal glucocorticoid receptor (GR-receptor) agonist;
- a selective β2 adrenoceptor agonist;
- a phosphodiesterase inhibitor;
- a protease inhibitor;
- a glucocorticoid;
- an anticholinergic agent;
- a modulator of chemokine receptor function; or
- an inhibitor of kinase function;

and instructions for the simultaneous, sequential or separate administration of the preparations to a patient in need thereof.

In one embodiment, the disclosure provides a pharmaceutical composition comprising a compound of Formula I, Ia, Ib, 1A-3A, or 1B-3B, or a pharmaceutically acceptable salt thereof, and at least one or more additional therapeutic agents. In particular embodiments, the at least one or more additional therapeutic agents is selected from the group consisting of glucocorticoid, beta-adrenoceptor agonist, anti-PD-1, anti-PD-L1, and anti-CTLA-4.

EXEMPLARY EMBODIMENTS

Embodiment I-1

A compound having the structure of Formula (I), or a pharmaceutically acceptable salt thereof, (I)

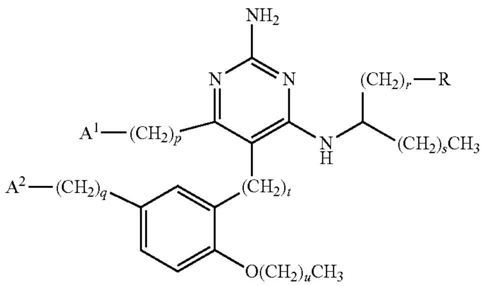

wherein

R is selected from the group consisting of —OH, $—SO_2CH_3$, $—NH_2$, —NHAc, and

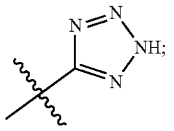 [SMILES: *c1nn[nH]n1]

$A^1$ is selected from the group consisting of

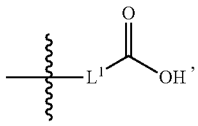
,
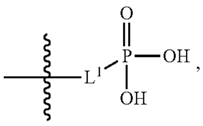
,
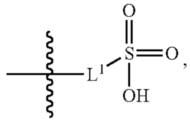
,
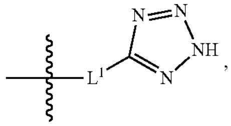
,
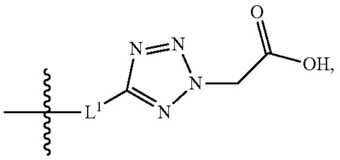

-continued

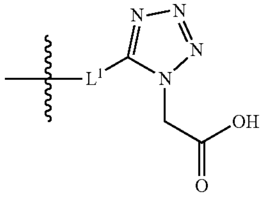
, and
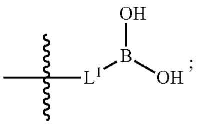
;

$A^2$ is selected from the group consisting of

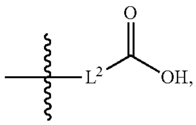
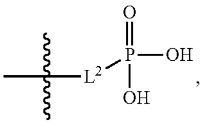
,
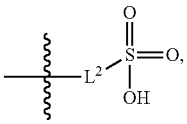
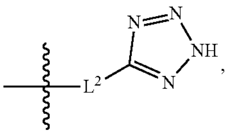
,
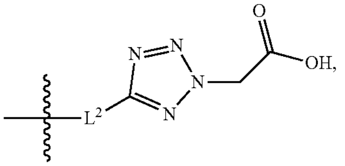
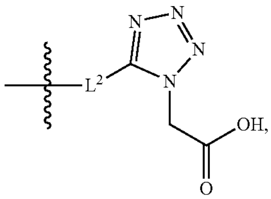
and
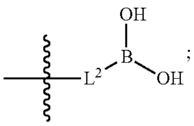
;

$L^1$ is a bond or $-(CH_2)_m-$;

$L^2$ is a bond or $-(CH_2)_n-$; and m, n, p, q, r, s, t, and u are independently selected from zero to four;

wherein if $A^1(CH_2)_p$ is $-CH_2CH_2C(=O)OH$, $A^2(CH_2)_q$ is $-CH_2C(=O)OH$, r is two, s is three, t is one and u is zero, then R cannot be $SO_2CH_3$.

Embodiment I-2

The compound of Embodiment I-1, or a pharmaceutically acceptable salt thereof, wherein the compound of Formula (I) is a compound of Formula (Ia) or Formula (Ib), (Ia)

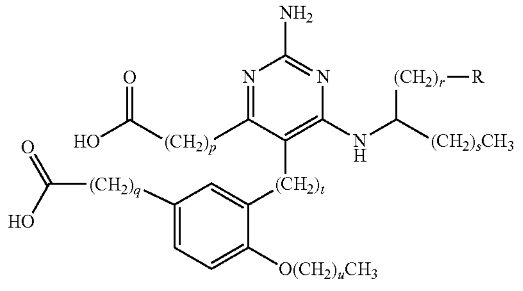

-continued (Ib)

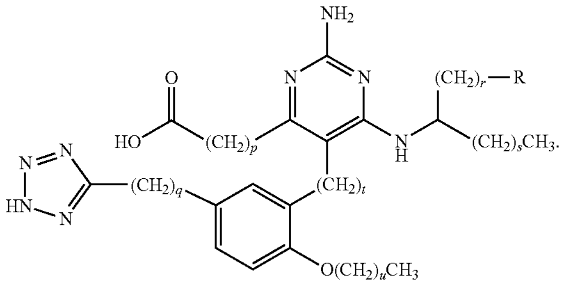

Embodiment I-3

The compound of Embodiment I-1 or I-2, or a pharmaceutically acceptable salt thereof, wherein p is 2 and q is 1.

Embodiment I-4

The compound of any one of Embodiments I-1 to I-3, or a pharmaceutically acceptable salt thereof, wherein R is —OH or $-SO_2CH_3$.

Embodiment I-5

The compound of any one of Embodiments I-1 to I-4, or a pharmaceutically acceptable salt thereof, wherein the compound is a single enantiomer.

Embodiment I-6

The compound of Embodiment I-1, or a pharmaceutically acceptable salt thereof, selected from the group consisting of:

| Compound | |
|---|---|
| 1B | 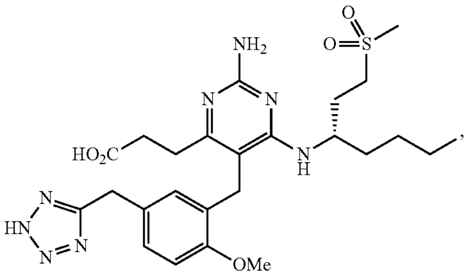 , |
| 2B | 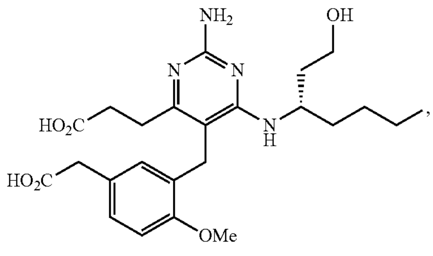 , and |

-continued

| Compound | |
|---|---|
| 3B | 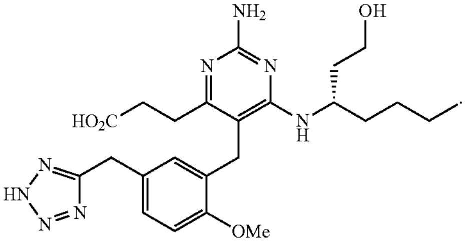 |

Embodiment I-7

A pharmaceutical composition comprising a compound of any one of Embodiments I-1 to I-6, or a pharmaceutically acceptable salt thereof, and a pharmaceutically acceptable carrier.

Embodiment I-8

The pharmaceutical composition of Embodiment I-7, wherein the pharmaceutically acceptable carrier is carboxy methylcellulose, saline, water, or another aqueous solution.

Embodiment I-9

The pharmaceutical composition of Embodiment I-7, comprising 0.1%-5% carboxy methylcellulose in water.

Embodiment I-10

The pharmaceutical composition of Embodiment I-7, further comprising at least one or more additional therapeutic agents.

Embodiment I-11

The pharmaceutical composition of Embodiment I-10, wherein the at least one or more additional therapeutic agents is selected from the group consisting of glucocorticoid, beta-adrenoceptor agonist, anti-PD-1, anti-PD-L1, and anti-CTLA-4.

Embodiment I-12

A method of treating a respiratory condition comprising administering to a subject in need thereof an effective amount of a compound of Formula (I), or a pharmaceutically acceptable salt thereof:

(I)

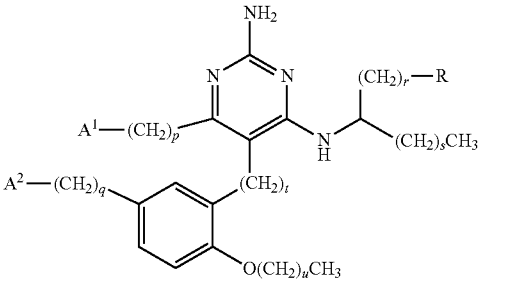

wherein

R is selected from the group consisting of —OH, —$SO_2CH_3$, —$NH_2$, —NHAc, and

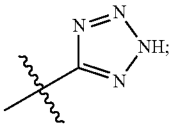 [SMILES: *c1nn[nH]n1]

$A^1$ is selected from the group consisting of

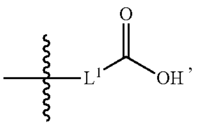 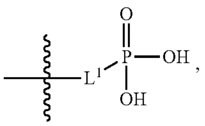

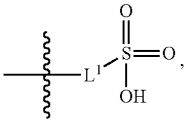 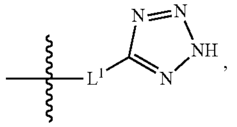

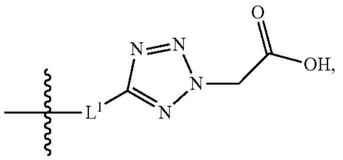

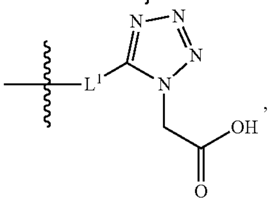 and 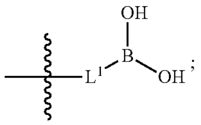

$A^2$ is selected from the group consisting of

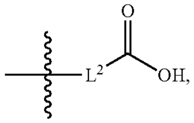 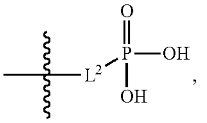

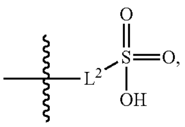 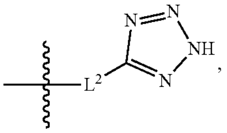

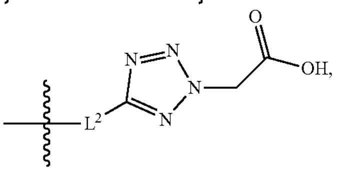

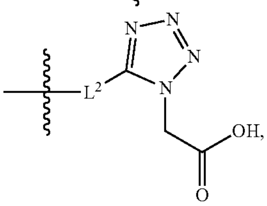 and 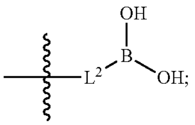

$L^1$ is a bond or $-(CH_2)_m-$;

$L^2$ is a bond or $-(CH_2)_n-$; and m, n, p, q, r, s, t, and u are independently selected from zero to four;

wherein if $A^1(CH_2)_p$ is $-CH_2CH_2C(=O)OH$, $A^2(CH_2)_q$ is $-CH_2C(=O)OH$, r is two, s is three, t is one and u is zero, then R cannot be $SO_2CH_3$.

Embodiment I-13

The method of Embodiment I-12, wherein the compound selected from the group consisting of

| Compound | |
|---|---|
| 1A | 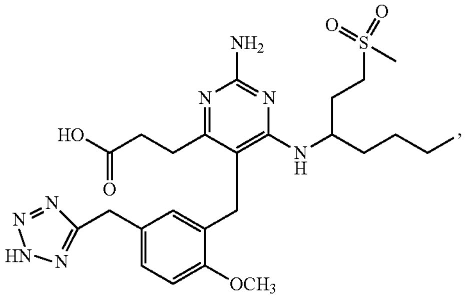 , |
| 2A | 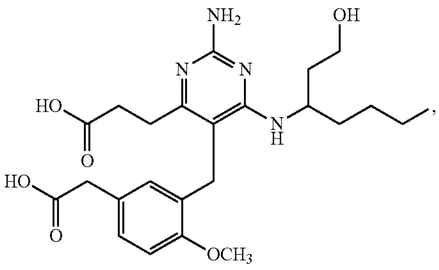 , and |
| 3A | 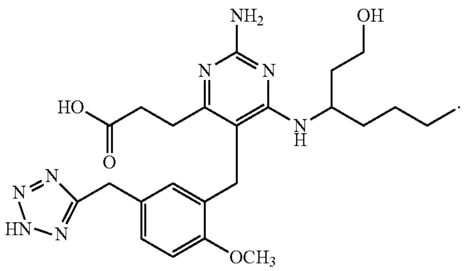 . |

or a pharmaceutically acceptable salt thereof.

Embodiment I-14

The method of Embodiment I-13, wherein the compound selected from the group consisting of

| Compound | |
|---|---|
| 1B | 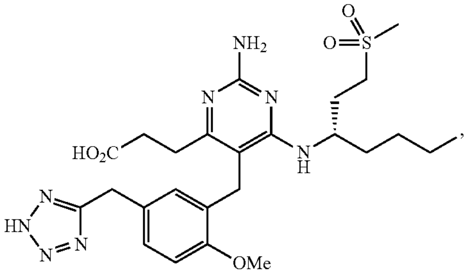 , |
| 2B | 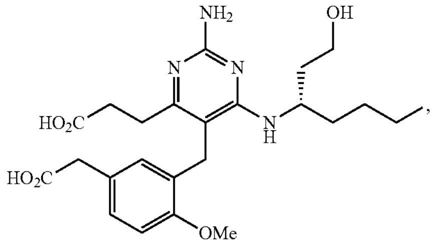 , and |
| 3B | 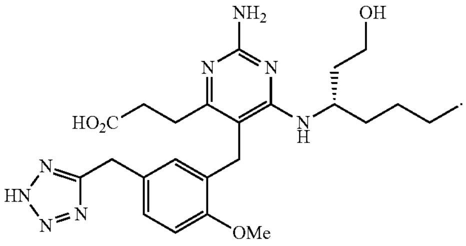 . |

or a pharmaceutically acceptable salt thereof.

Embodiment I-15

A method of treating a respiratory condition comprising administering to the subject an effective amount of a pharmaceutical composition of any one of Embodiments I-7 to I-11.

Embodiment I-16

The method of any one of Embodiments I-12 to I-15, wherein the respiratory condition is cancer.

Embodiment I-17

The method of Embodiment I-16, wherein the cancer is selected from the group consisting of lung cancer; head and neck cancer; ear, nose, or throat cancer; and cancers of the upper or lower airways.

Embodiment I-18

The method of Embodiment I-16, wherein the cancer is lung cancer.

Embodiment I-19

The method of any one of Embodiments I-12 to I-15, wherein the respiratory condition is a non-cancerous disease.

Embodiment I-20

The method of Embodiment I-18, wherein the respiratory condition is selected from the group consisting of asthma, allergy, and COPD.

Embodiment I-21

The method of any one of Embodiments I-12 to I-15, wherein the respiratory condition is an aerodigestive condition.

Embodiment I-22

The method of any one of Embodiments I-12 to I-21, wherein the administration is intranasal or intratracheal.

Embodiment I-23

The method of any one of Embodiments I-12 to I-21, wherein the subject inhales the compound.

Embodiment I-24

The method of any one of Embodiments I-12 to I-23, wherein the compound is administered in combination with one or more additional therapeutic agents.

Embodiment I-25

The method of Embodiment I-24, wherein the one or more additional therapeutic agents is selected from the group consisting of glucocorticoid, a beta-adrenoceptor agonist, anti-PD-1, anti-PD-L1, and anti-CTLA-4.

Embodiment I-26

A compound of any one of Embodiments I-1 to I-6, or a pharmaceutically acceptable salt thereof, for use in therapy.

Embodiment I-27

A compound of any one of Embodiments I-1 to I-6, or a pharmaceutically acceptable salt thereof, for use in treating a respiratory disease.

Embodiment I-28

A compound of any one of Embodiments I-1 to I-6, or a pharmaceutically acceptable salt thereof, for use in treating lung cancer.

Embodiment I-29

Use of a compound of any one of Embodiments I-1 to I-6, or a pharmaceutically acceptable salt thereof, in the manufacture of a medicament.

Embodiment I-30

The use according to Embodiment I-29, wherein the medicament is used to treat a respiratory disease.

Embodiment I-31

The use according to Embodiment I-29, wherein the medicament is used to treat lung cancer.

Embodiment I-32

A pharmaceutical composition of any one of Embodiments I-7 to I-11 for use in therapy.

Embodiment I-33

A pharmaceutical composition of any one of Embodiments I-7 to I-11 for use in treating a respiratory disease.

Embodiment I-34

A pharmaceutical composition of any one of Embodiments I-7 to I-11 for use in treating lung cancer.

Embodiment II-1

A compound having the structure of Formula (I), or a pharmaceutically acceptable salt thereof, (I)

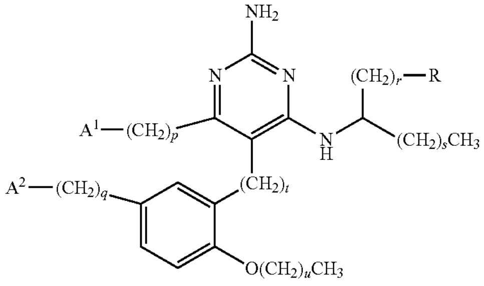

wherein

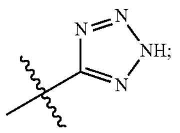 [SMILES: *c1nn[nH]n1]

R is selected from the group consisting of —OH, —$SO_2CH_3$, —$NH_2$, —NHAc, and $A^1$ is selected from the group consisting of

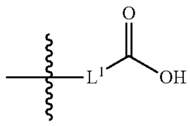, 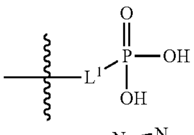,

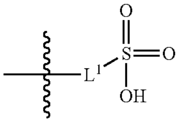, 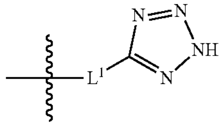,

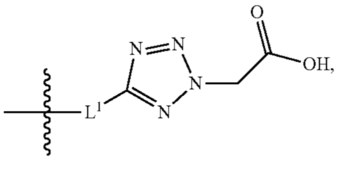

-continued

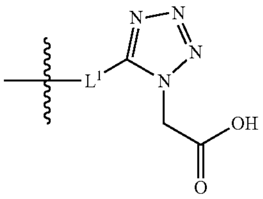

, and

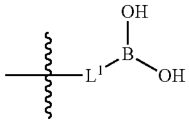

;

$A^2$ is selected from the group consisting of

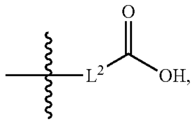

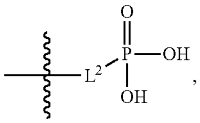

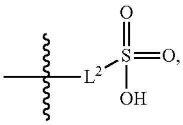

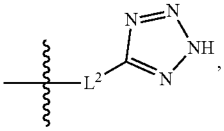

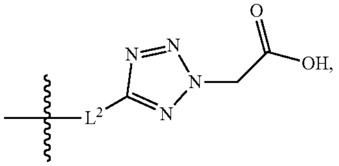

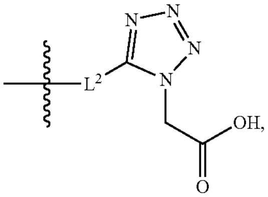

and

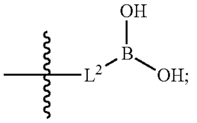

$L^1$ is a bond or $-(CH_2)_m-$;

$L^2$ is a bond or $-(CH_2)_n-$; and m, n, p, q, r, s, t, and u are independently selected from zero to four;

wherein if $A^1(CH_2)_p$ is $-CH_2CH_2C(=O)OH$, $A^2(CH_2)_q$ is $-CH_2C(=O)OH$, r is two, s is three, t is one and u is zero, then R is —OH, $-NH_2$, —NHAc, or

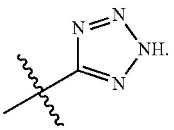 [SMILES: *c1nn[nH]n1]

Embodiment II-2

The compound of Embodiment II-1, or a pharmaceutically acceptable salt thereof, wherein the compound of Formula (I) is a compound of Formula (Ia) or Formula (Ib), (Ia)

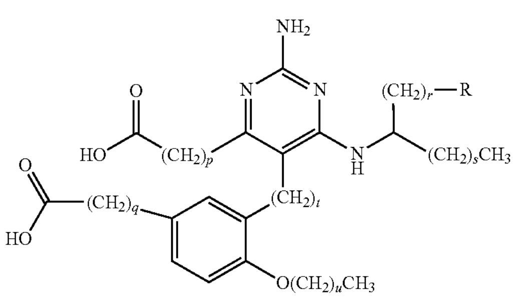

(Ib)

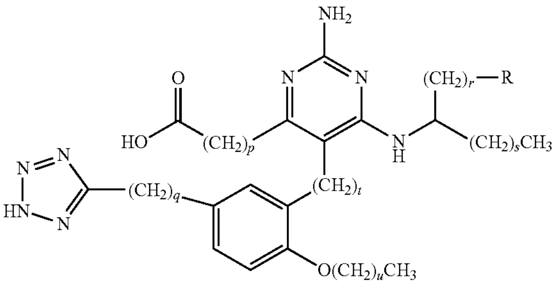

wherein R is selected from the group consisting of —OH, $-SO_2CH_3$, $-NH_2$, —NHAc, and

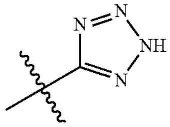 [SMILES: *c1nn[nH]n1]

and p, q, r, s, t, and u are independently selected from zero to four;

wherein if the compound is a compound of Formula (Ia), and p is two, q is one, r is two, s is three, t is one and u is zero, then R is —OH, $-NH_2$, —NHAc, or

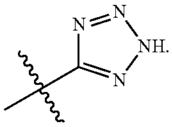 [SMILES: *c1nn[nH]n1]

Embodiment II-3

The compound of Embodiment II-1 or II-2, or a pharmaceutically acceptable salt thereof, wherein p is 2 and q is 1.

Embodiment II-4

The compound of any one of Embodiments II-1 to II-3, or a pharmaceutically acceptable salt thereof, wherein R is —OH.

Embodiment II-5

The compound of any one of Embodiments II-1 to II-3, or a pharmaceutically acceptable salt thereof, wherein R is —$SO_2CH_3$, wherein if the compound is a compound of Formula (Ia), and p is two, q is one, r is two, s is three, t is one and u is zero, then R is —OH, —$NH_2$, —NHAc, or

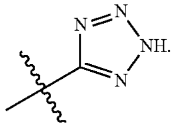 [SMILES: *c1nn[nH]n1]

Embodiment II-6

The compound of any one of Embodiments II-1 to II-5, or a pharmaceutically acceptable salt thereof, wherein the compound is a single enantiomer.

Embodiment II-7

The compound of Embodiment II-1, or a pharmaceutically acceptable salt thereof, selected from the group consisting of:

1B

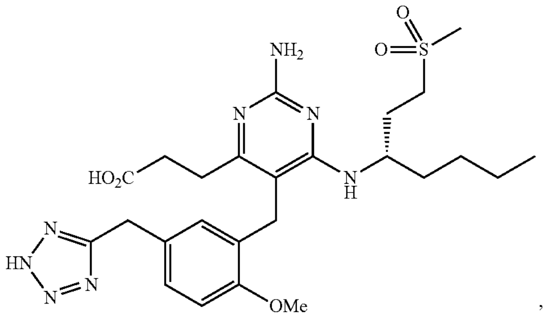

,

2B

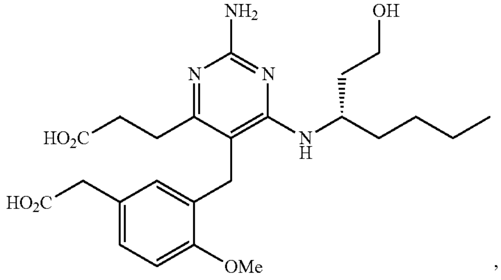

, and

3B

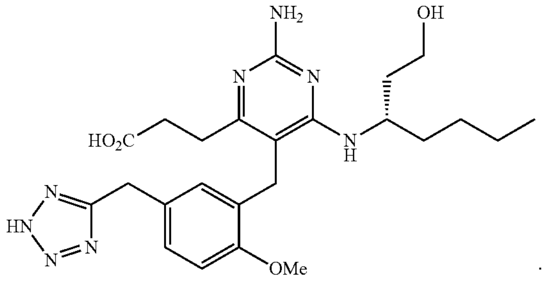

.

Embodiment II-8

A pharmaceutical composition comprising a compound of any one of Embodiments II-1 to II-7, or a pharmaceutically acceptable salt thereof, and a pharmaceutically acceptable carrier.

Embodiment II-9

The pharmaceutical composition of Embodiment II-8, wherein the pharmaceutically acceptable carrier is carboxy methylcellulose, saline, water, or another aqueous solution.

Embodiment II-10

The pharmaceutical composition of Embodiment II-8 or II-9, comprising 0.1%-5% carboxy methylcellulose in water.

Embodiment II-11

The pharmaceutical composition of any one of Embodiments II-8 to II-10, further comprising at least one or more additional therapeutic agents.

Embodiment II-12

The pharmaceutical composition of Embodiment II-11, wherein the at least one or more additional therapeutic agents is selected from the group consisting of glucocorticoid, beta-adrenoceptor agonist, anti-PD-1, anti-PD-L1, and anti-CTLA-4.

Embodiment II-13

The pharmaceutical composition of any one of Embodiments II-8 to II-12, wherein the pharmaceutical composition is formulated for inhalation.

Embodiment II-14

A method of treating a respiratory condition comprising administering to a subject in need thereof an effective amount of a compound of Formula (I), or a pharmaceutically acceptable salt thereof:

(I)

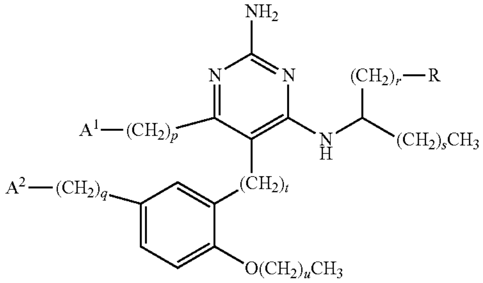

wherein

R is selected from the group consisting of —OH, —$SO_2CH_3$, —$NH_2$, —NHAc, and

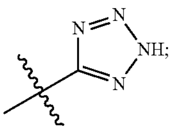 [SMILES: *c1nn[nH]n1]

$A^1$ is selected from the group consisting of

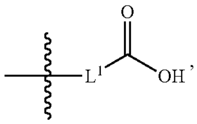,
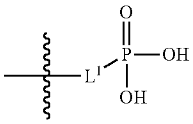,
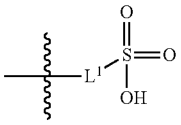,
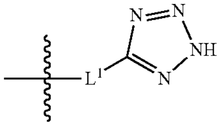,
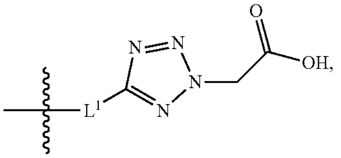
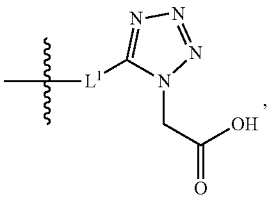, and
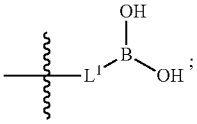;

$A^2$ is selected from the group consisting of

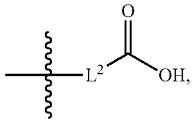
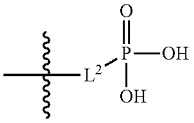,
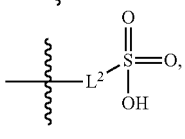
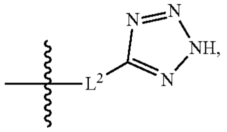
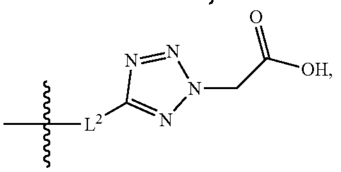
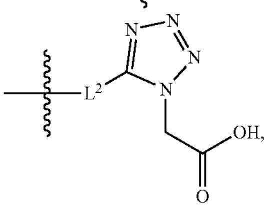 and
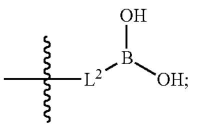

$L^1$ is a bond or $-(CH_2)_m-$;

$L^2$ is a bond or $-(CH_2)_n-$; and m, n, p, q, r, s, t, and u are independently selected from zero to four;

wherein if $A^1(CH_2)_p$ is $-CH_2CH_2C(=O)OH$, $A^2(CH_2)_q$ is $-CH_2C(=O)OH$, r is two, s is three, t is one and u is zero, then R is $-OH$, $-NH_2$, $-NHAc$, or

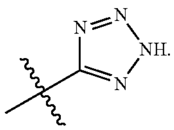 [SMILES: *c1nn[nH]n1]

Embodiment II-15

The method of Embodiment II-14, wherein the compound of Formula (I), or a pharmaceutically acceptable salt thereof, is selected from the group consisting of

| Compound | |
|---|---|
| 1A | 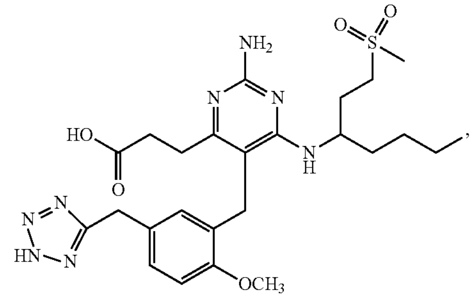 |
| 2A | 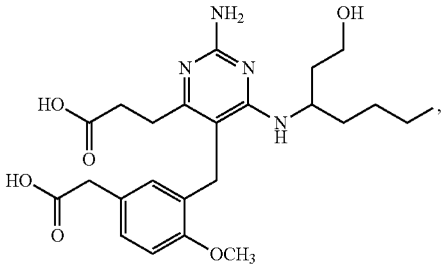, and |
| 3A | 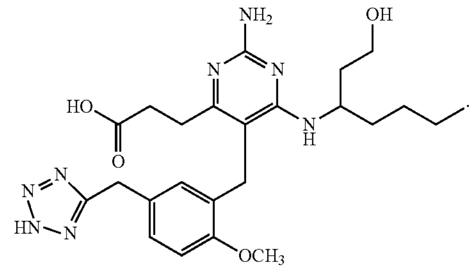 |

or a pharmaceutically acceptable salt thereof.

Embodiment II-16

The method of Embodiment II-14 or II-15, wherein the compound of Formula (I), or a pharmaceutically acceptable salt thereof, is selected from the group consisting of

| Compound | |
|---|---|
| 1B | 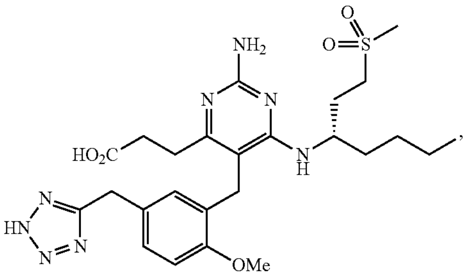, |
| 2B | 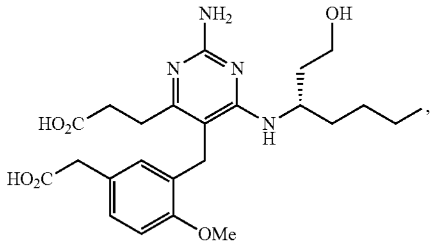, and |
| 3B | 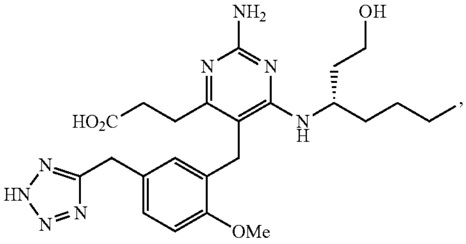, |

or a pharmaceutically acceptable salt thereof.

Embodiment II-17

A method of treating a respiratory condition comprising administering to the subject an effective amount of a pharmaceutical composition of any one of Embodiments II-8 to II-13.

Embodiment II-18

The method of any one of Embodiments II-14 to II-17, wherein the respiratory condition is cancer.

Embodiment II-19

The method of Embodiment II-18, wherein the cancer is selected from the group consisting of lung cancer; head and neck cancer; ear, nose, or throat cancer; and cancers of the upper or lower airways.

Embodiment II-20

The method of Embodiment II-18 or II-19, wherein the cancer is lung cancer.

Embodiment II-21

The method of any one of Embodiments II-14 to II-17, wherein the respiratory condition is a non-cancerous disease.

Embodiment II-22

The method of any one of Embodiments II-14 to II-17 or II-21, wherein the respiratory condition is selected from the group consisting of asthma, allergy, and COPD.

Embodiment II-23

The method of any one of Embodiments II-14 to II-17 or II-21, wherein the respiratory condition is an aerodigestive condition.

Embodiment II-24

The method of any one of Embodiments II-14 to II-23, wherein the administration is intranasal or intratracheal.

Embodiment II-25

The method of any one of Embodiments II-14 to II-24, wherein the subject inhales the compound.

Embodiment II-26

The method of any one of Embodiments II-14 to II-25, wherein the compound is administered in combination with one or more additional therapeutic agents.

Embodiment II-27

The method of Embodiment II-26, wherein the one or more additional therapeutic agents is selected from the group consisting of glucocorticoid, a beta-adrenoceptor agonist, anti-PD-1, anti-PD-L1, and anti-CTLA-4.

Embodiment II-28

A compound of any one of Embodiments II-1 to II-7, or a pharmaceutically acceptable salt thereof, for use in therapy.

Embodiment II-29

A compound of any one of Embodiments II-1 to II-7, or a pharmaceutically acceptable salt thereof, for use in treating a respiratory condition.

Embodiment II-30

Use of a compound of any one of Embodiments II-1 to II-7, or a pharmaceutically acceptable salt thereof, in the manufacture of a medicament.

Embodiment II-31

The use according to Embodiment II-30, wherein the medicament is used to treat a respiratory condition.

Embodiment II-32

A pharmaceutical composition of any one of Embodiments II-8 to II-13 for use in therapy.

Embodiment II-33

A pharmaceutical composition of any one of Embodiments II-8 to II-12 for use in treating a respiratory condition.

Embodiment II-34

The compound for use of Embodiment II-29, the use of Embodiment II-31, or the pharmaceutical composition of Embodiment II-33, wherein the respiratory condition is cancer.

Embodiment II-35

The compound for use, the use, or the pharmaceutical composition of Embodiment II-34, wherein the cancer is selected from the group consisting of lung cancer; head and neck cancer; ear, nose, or throat cancer; and cancers of the upper or lower airways.

Embodiment II-36

The compound for use, the use, or the pharmaceutical composition of Embodiment II-34 or II-35, wherein the cancer is lung cancer.

Embodiment II-37

The compound for use of Embodiment II-29, the use of Embodiment II-31, or the pharmaceutical composition of Embodiment II-33, wherein the respiratory condition is a non-cancerous disease.

Embodiment II-38

The compound for use of Embodiment II-29, the use of Embodiment II-31, or the pharmaceutical composition of Embodiment II-33, wherein the respiratory condition is selected from the group consisting of asthma, allergy, and COPD.

Embodiment II-39

The compound for use of Embodiment II-29, the use of Embodiment II-31, or the pharmaceutical composition of Embodiment II-33, wherein the respiratory condition is an aerodigestive condition.

Embodiment II-40

The compound for use, the use, or the pharmaceutical composition of any one of Embodiments II-28 to II-39, wherein compound or pharmaceutical composition is formulated for intranasal or intratracheal administration.

Embodiment II-41

The compound for use, the use, or the pharmaceutical composition of any one of Embodiments II-28 to II-40, wherein compound or pharmaceutical composition is formulated for inhalation.

Embodiment II-42

The compound for use, the use, or the pharmaceutical composition of any one of Embodiments II-28 to II-41, wherein compound or pharmaceutical composition is formulated for administration with one or more additional therapeutic agents.

Embodiment II-43

The compound for use, the use, or the pharmaceutical composition of Embodiment II-42, wherein the one or more additional therapeutic agents is selected from the group consisting of glucocorticoid, a beta-adrenoceptor agonist, anti-PD-1, anti-PD-L1, and anti-CTLA -4.

EXAMPLES

The following examples are provided to illustrate the present disclosure, and should not be construed as limiting thereof. In these examples, all parts and percentages are by weight, unless otherwise noted. Abbreviations in the examples are noted below.

Abbreviations

| | |
|---|---|
| AIBN | azobisisobutyronitrile |
| aq. | aqueous |
| DCM | dichloromethane |
| DMAP | 4-dimethylaminopyridine |
| EA | ethyl acetate |
| Eq | equivalent |
| h or hr | hour |
| HPLC | high performance liquid chromatography |
| LC-MS | liquid chromatography mass spectrometry |
| min | minutes |
| NBS | N-bromosuccinimide |
| NMP | N-methylpyrrolidine |
| NMR | nuclear magnetic resonance |
| PE | petroleum ether |
| prep | preparative |
| rt or r.t. | room temperature |
| sat. | saturated |
| TBAF | tetrabutylammonium flouride |
| TBS | tert-butyldimethylsilyl |
| TEA | triethylamine |
| TFA | trifluoroacetic acid |
| THF | tetrahydrofuran |
| TLC | thin layer chromatography |
| HPLC | high performance liquid chromatography |
| LC-MS | liquid chromatography mass spectrometry |

CHEMISTRY SYNTHESIS EXAMPLES

Synthesis Example 1A: Synthesis of Intermediate: 3-(2-amino-6-chloro-5-(5-(cyanomethyl)-2-methoxybenzyl)pyrimidin-4-yl)propanoic acid dichloro(methoxy)methane

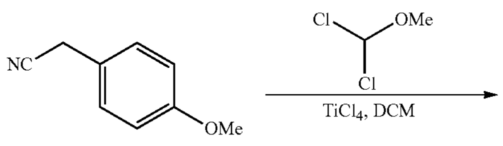

2-(4-methoxyphenyl)acetontrile diethyl 3-oxohexanedioate

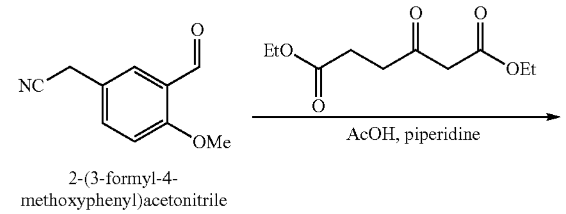

2-(3-formyl-4-methoxyphenyl)acetonitrile

-continued

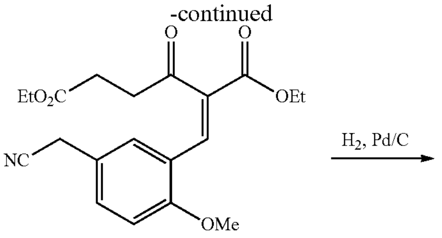

diethyl (E)-2-(5-(cyanomethyl)-2-methoxybenzylidene)-3-oxohexanedioate

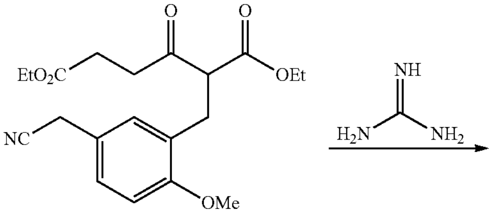

diethyl 2-(5-(cyanomethyl)-2-methoxybenzyl)-3-oxohexanedioate

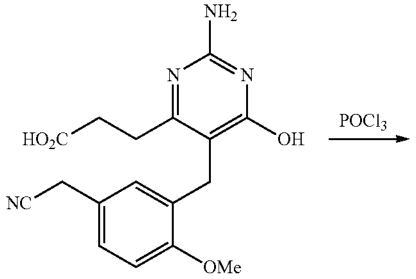

3-(2-amino-5-(5-(cyanomethyl)-2-methoxybenzyl)-6-hydroxypyrimidin-4-yl)propanoic acid

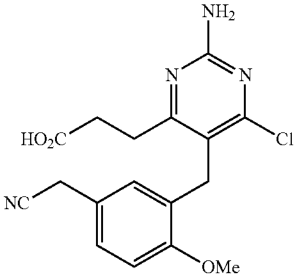

3-(2-amino-6-chloro-5-(5-(cyanomethyl)-2-methoxybenzyl)pyrimidin-4-yl)propanoic acid
Chemical Formula: $C_{17}H_{17}ClN_4O_3$
Exact Mass: 360.10

Step 1: 2-(3-formyl-4-methoxyphenyl)acetonitrile

To a solution of 2-(4-methoxyphenyl)acetonitrile (1.0 eq), dichloro(methoxy)methane (1.3 eq) in anhydrous DCM (0.2M) was added $TiCl_4$ (2.0 eq) at 0° C. under nitrogen. The reaction was stirred for 30 min at 0° C. and then quenched with 2.5N HCl. The organic layer was dried and concentrated to give the title compound as light yellow solid.

Step 2: diethyl (E)-2-(5-(cyanomethyl)-2-methoxybenzylidene)-3-oxohexanedioate

To a solution of 2-(3-formyl-4-methoxyphenyl)acetonitrile (1.0 eq) and diethyl 3-oxohexanedioate (1.2 eq) in toluene (0.4M) was added catalytic amount of piperidine and acetic acid. The reaction mixture was heated at 150° C. for 3 days and then concentrated to give the title compound as a crude product.

Step 3: diethyl 2-(5-(cyanomethyl)-2-methoxybenzyl)-3-oxohexanedioate

A solution of diethyl (E)-2-(5-(cyanomethyl)-2-methoxybenzylidene)-3-oxohexanedioate was stirred under hydrogen atmosphere in presence of 50% wet Pd/C (4% weight equivalent) in EA (0.4M) at 50° C. for 16 hr. Pd/C was filtered off, and the filtrate was concentrated. The residue was purified by column chromatography (PE/EA=20:1) to give the title compound.

Step 4: 3-(2-amino-5-(5-(cyanomethyl)-2-methoxybenzyl)-6-hydroxypyrimidin-4-yl)propanoic acid A mixture of diethyl 2-(5-(cyanomethyl)-2-methoxybenzyl)-3-oxohexanedioate (1.0 eq) in MeOH (0.3M) and guanidine carbonate (2.0 eq) was stirred at 85° C. for 16 hr. The precipitate was collected by filtration. The solid was washed with water and dried in vacuum to give the title compound as a white solid.

Step 5: 3-(2-amino-6-chloro-5-(5-(cyanomethyl)-2-methoxybenzyl)pyrimidin-4-yl)propanoic acid A solution of 3-(2-amino-5-(5-(cyanomethyl)-2-methoxybenzyl)-6-hydroxypyrimidin -4-yl)propanoic acid in $POCl_3$ (0.3M) was stirred at 100° C. for 1 hr under nitrogen. The reaction was cooled to rt, and the solvent was evaporated under reduced pressure. The residue was diluted with water, and pH was adjusted to 7 by addition of solid $NaHCO_3$. The mixture was stirred at 50° C. for 1 hr and then cooled to rt. The precipitate was collected by filtration. The filter cake was washed with water, dried in vacuum to give the title compound as a white solid. $^1H$ NMR (400 MHz, DMSO) δ 7.18 (d, J=8.0 Hz, 1H), 7.02 (d, J=8.0 Hz, 1H), 6.66 (s, 1H), 3.87-3.80 (m, 7H), 2.62-2.55 (m, 4H).

Synthesis Example 1B: Synthesis of Intermediate: (S)-1-(methylthio)heptan-3-amine tert-butyl 2-(triphenyl-$\lambda^5$-phosphanylidene)acetate

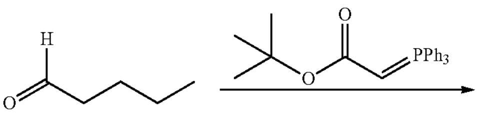

pentanal (S)-N-benzyl-1-phenylethan-1-amine

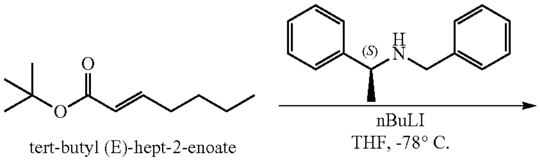

tert-butyl (E)-hept-2-enoate

-continued

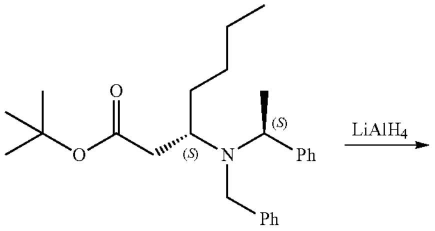

tert-butyl (S)-3-(benzyl((S)-1-phenylethyl)amino)heptanoate

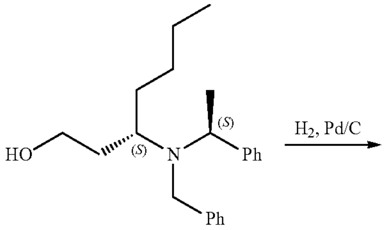

(S)-3-(benzyl((S)-1-phenylethyl)amino)heptan-1-ol

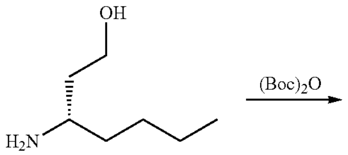

(S)-3-aminoheptan-1-ol

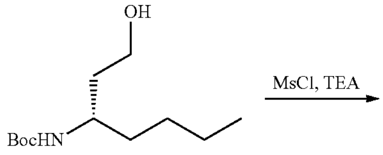

tert-butyl (S)-(1-hydroxyheptan-3-yl)carbamate

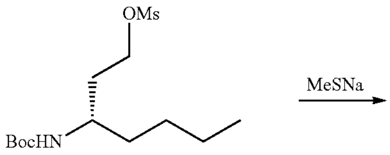

(S)-3-((tert-butoxycrbonyl)amino)heptyl methanesulfonate

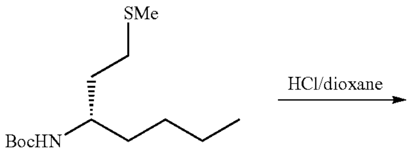

tert-butyl (S)-(1-(methylthio)heptan-3-yl)carbamate

-continued

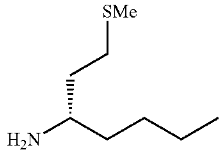

(S)-1-(methylthio)heptan-3-amine
Chemical Formula: $C_8H_{19}NS$
Exact Mass: 161.12

Step 1: tert-butyl (E)-hept-2-enoate

A mixture of pentanal (1.0 eq) and tert-butyl 2-(triphenyl-$\lambda^5$-phosphanylidene)acetate (1.05 eq) in THF (1M) was stirred at 50° C. for 16 hr. The mixture was concentrated under reduced pressure, and PE was added. The solids were filtered off, and the filtrate was evaporated to dryness. The crude residue was purified by flash column chromatography (eluent: PE to PE/EA=100:1) to give the title compound as a yellow oil.

Step 2: tert-butyl (S)-3-(benzyl((S)-1-phenylethyl)amino)heptanoate

To a solution of (S)—N-benzyl-1-phenylethan-1-amine (1.3 eq) in THF (0.9M) at −78° C. was added dropwise 2.5M n-BuLi (1.2 eq) over 20 min. The mixture was stirred at −78° C. for 10 min, then tert-butyl (E)-hept-2-enoate (1.0 eq) in THF (0.7M) was added dropwise. The resulting mixture was stirred at −78° C. for 30 min, then quenched with aq. $NH_4C1$ and extracted with EA. The organic layer was dried over $Na_2SO_4$, filtered, and concentrated under reduced pressure. The residue was purified by flash column chromatography (eluent: PE to PE/EA=100:1) to give the title compound as a yellow oil.

Step 3: (S)-3-(benzyl((S)-1-phenylethyl)amino)heptan-1-ol

To a solution of tert-butyl (S)-3-(benzyl((S)-1-phenylethyl)amino)heptanoate (1.0 eq) in anhydrous THF (0.4M) at 0° C. was added portion-wise $LiAlH_4$ (1.6 eq). After the addition, the mixture was stirred at r.t. for 5 hr. The mixture was quenched with 1.0 M NaOH solution, filtered, and the filtrate was extracted with EA. The organic layer was dried over $Na_2SO_4$, concentrated under reduced pressure. The residue was purified by flash column chromatography (eluent: PE to PE/EA=5:1) to give the title compound as a yellow oil.

Step 4: (S)-3-aminoheptan-1-ol

To a solution of (S)-3-(benzyl((S)-1-phenylethyl)amino)heptan-1-ol (1.0 eq) in MeOH (0.1M) was stirred at 50° C. for 48 hr under H2 atmosphere in presence of Pd/C (10% wt). The mixture was filtered, and the filtrate was concentrated under reduced pressure to give the title compound as a brown oil.

Step 5: tert-butyl (S)-(1-hydroxyheptan-3-yl)carbamate

To a solution of (S)-3-aminoheptan-1-ol (1.0 eq) in 1:1 dioxane/$H_2O$ (0.5M) at 0° C. was added NaOH (1.2 eq) and $Boc_2O$ (1.2 eq) and warmed to rt. After the reaction was competed, the mixture was partitioned between $H_2O$/EA. The organic layer was dried over $Na_2SO_4$, concentrated under reduced pressure. The residue was purified by flash column chromatography (eluent: PE to PE/EA=3:1) to give the title compound as white solid.

Step 6: (S)-3-((tert-butoxycarbonyl)amino)heptyl methanesulfonate

A mixture of tert-butyl (S)-(1-hydroxyheptan-3-yl)carbamate (1.0 eq) and TEA (1.2 eq) in DCM (0.4M) was added dropwise methanesulfonyl chloride (1.1 eq.) and stirred at 0° C. for 1 hr. The resulting mixture was partitioned between EA and water. The organic layer was dried over $Na_2SO_4$, concentrated under reduced pressure to give the title compound as a brown oil.

Step 7: tert-butyl (S)-(1-(methylthio)heptan-3-yl) carbamate

A mixture of (S)-3-((tert-butoxycarbonyl)amino)heptyl methanesulfonate (1.0 eq) in DMF (0.7M) and MeSNa (2.0 eq) was stirred at 70° C. for 16 hr. The resulting mixture was partitioned between EA and water. The organic layer was dried over $Na_2SO_4$, concentrated under reduced pressure. The residue was purified by flash column chromatography (eluent: PE to PE/EA=10:1) to give the title compound as a yellowish oil.

Step 8: (S)-1-(methylthio)heptan-3-amine

To a solution of tert-butyl (S)-(1-(methylthio)heptan-3-yl)carbamate (1.0 eq) in DCM (0.5M) was added excess 4M HCl/dioxane (1/3 volume equivalent). The resulting mixture was stirred at r.t. for 16 hr, concentrated under reduced pressure. The residue was triturated with $Et_2O$ and the precipitated solid was collected by filtration to give the title compound as a white solid (HCl salt). LC-MS: $[M+H]^+$=162 $^1H$ NMR (400 MHz, $CDCl_3$) δ 8.43 (br s, 3H), 3.41-3.38 (m, 1H), 2.71 (t, J=6.8 Hz, 2H), 2.13 (s, 3H), 2.11-2.03 (m, 1H), 2.00-1.91 (m, 1H), 1.82-1.66 (m, 2H), 1.52-1.32 (m, 4H), 0.92 (t, J=7.2 Hz, 3H).

Synthesis Example 1C: Synthesis of Intermediate: (S)-1-((tert-butyldimethylsilyl)oxy)heptan-3-amine

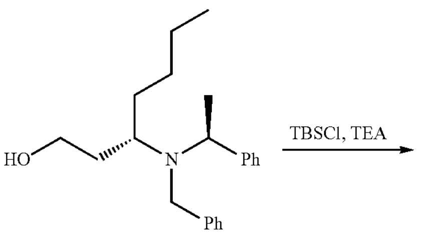

(S)-3-(benzyl((S)-1-phenylethyl)amino)heptan-1-ol

-continued

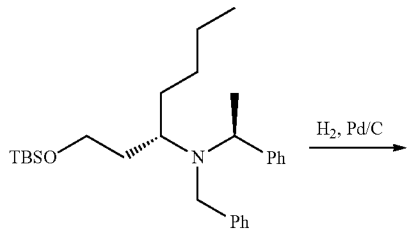

(S)-N-benxyl-1-((tert-butyldimethylsilyl)oxy)-N-((S)-1-phenylethyl)heptan-3-amine

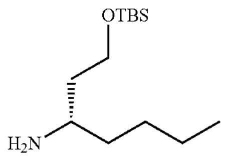

(S)-1-((tert-butyldimethylsilyl)oxy)heptan-3-amine
Chemical Formula: $C_{13}H_{31}NOSi$
Exact Mass: 245.22

Step 1: (S)—N-benzyl-1-((tert-butyldimethylsilyl) oxy)-N—((S)-1-phenylethyl)heptan-3-amine To a solution of (S)-3-(benzyl((S)-1-phenylethyl)amino) heptan-1-ol (1.0 eq) in DCM (0.3M) was added TEA (1.5 eq) and TBSCl (1.2 eq) at 0° C. The reaction was warmed to r.t. over 16 hr. The reaction was quenched with water, and the organic layer was dried, concentrated, and purified by column chromatography (PE:EA=100:1 to 10:1) to give the title compound.

Step 2: (S)-1-((tert-butyldimethylsilyl)oxy)heptan-3-amine

To a solution of (S)—N-benzyl-1-((tert-butyldimethylsilyl)oxy)-N—((S)-1-phenylethyl)heptan-3-amine (1.0 eq) in MeOH (0.24M) was added 50% wet Pd/C (10% wt). The solution was stirred under hydrogen atmosphere at 50° C. for 16 hr. The solid was filtered, and the filtrate was concentrated to give the title compound as light yellow oil. $^1H$ NMR (400 MHz, $CDCl_3$) δ 3.74-3.70 (m, 2H), 2.85-2.83 (m, 1H), 1.64-1.27 (m, 8H), 0.85-0.91 (m, 12H), 0.07 (s, 6H).

Synthesis Example 2: Synthesis of Compound 1B, (S)-3-(5-(5-((2H-tetrazol-5-yl)methyl)-2-methoxy-benzyl)-2-amino-6-((1-(methyl-sulfonyl)heptan-3-yl) amino)pyrimidin-4-yl)propanoic acid (S)-1-(methylthio)heptan-3-amine

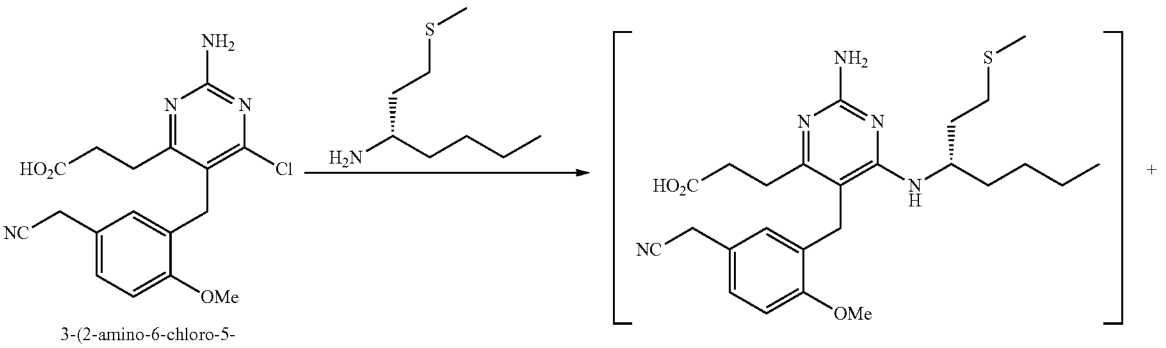

3-(2-amino-6-chloro-5-(5-(cyanomethyl)-2-methoxybenzyl)pyrimidin-4-yl)propanoic acid

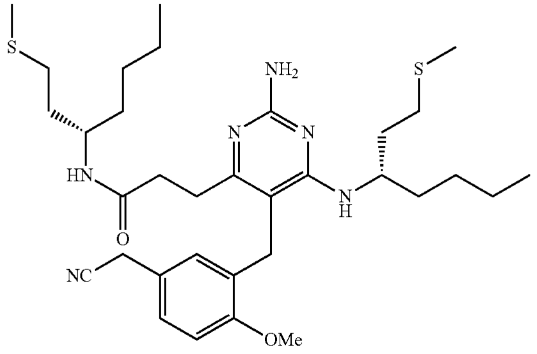

3-(2-amino-5-(5-(cyanomethyl)-2-methoxybenzyl)-6-(((S)-1-(methylthio)heptan-3-yl)amino)pyrimidin-4-yl)-N-((S)-1-(methylthio)heptan-3-yl)propanamide

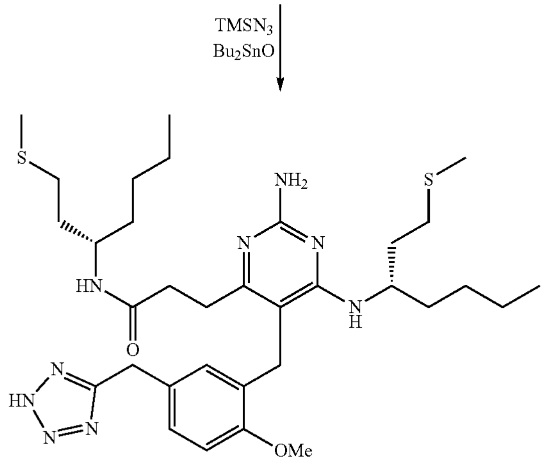

3-(5-(5-((2H-tetrazol-5-yl)methyl)-2-methoxybenzyl)-2-amino-6-(((S)-1-(methylthio)heptan-3-yl)amino)pyrimidin-4-yl)-N-((S)-1-(methylthio)heptan-3-yl)propanamide 3-(5-(5-((2H-tetrazol-5-yl)methyl)-2-methoxybenzyl)-2-amino-6-(((S)-1-(methylsulfonyl)heptan-3-yl)amino)pyrimidin-4-yl)-N-((S)-1-(methylthio)heptan-3-yl)propanamide

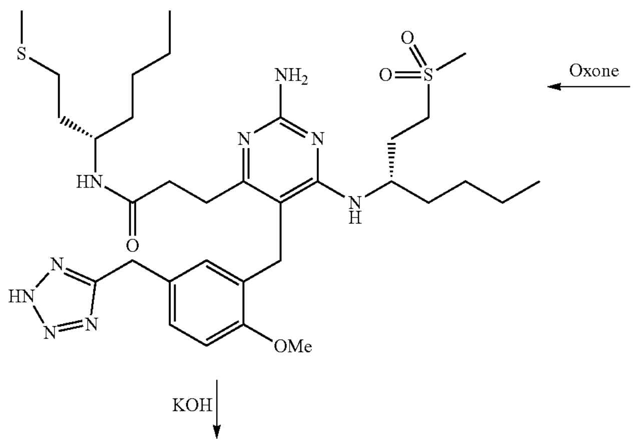

-continued

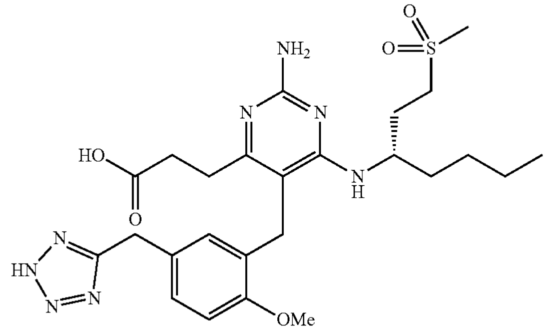

(S)-3-(5-(5-((2H-tetrazol-5-yl)methyl)-2-methoxybenzyl)-2-amino-6-((1-(methylsulfonyl)heptan-3-yl)amino)pyrimidin-4-yl)propanoic acid
Chemical Formula: $C_{25}H_{36}N_8O_5S$
Exact Mass: 560.25

Step 1: 3-(2-amino-5-(5-(cyanomethyl)-2-methoxybenzyl)-6-(((S)-1-(methylthio)heptan-3-yl)amino)pyrimidin-4-yl)-N—((S)-1-(methylthio)heptan-3-yl)propanamide 3-(2-amino-6-chloro-5-(5-(cyanomethyl)-2-methoxybenzyl)pyrimidin-4-yl)propanoic acid (1.0 eq) in neat (S)-1-(methylthio)heptan-3-amine (2.0 eq) was stirred for 6 hr at 100° C. under Ar atmosphere. The mixture was partitioned between DCM and 1N citric acid. The organic layer was dried over $Na_2SO_4$, concentrated and purified by column chromatography (eluent DCM/MeOH=100:1 to 20:1) to give the title compound. The mono-substituted compound was also isolated.

Step 2: 3-(5-(5-((2H-tetrazol-5-yl)methyl)-2-methoxybenzyl)-2-amino-6-(((S)-1-(methyl-thio) heptan -3-yl)amino)pyrimidin-4-yl)-N—((S)-1-(methylthio)heptan-3-yl)propanamide A mixture of 3-(2-amino-5-(5-(cyanomethyl)-2-methoxybenzyl)-6-(((S)-1-(methylthio)heptan-3-yl)amino)pyrimidin-4-yl)-N—((S)-1-(methylthio)heptan-3-yl)propanamide (1.0 eq) in dioxane (0.07M) was added $Bu_2SnO$ (2.0 eq) and $TMSN_3$ (5.0 eq). The mixture was stirred at 120° C. for 5 hr under $N_2$, and then concentrated to give the title compound, which was used in the next step without further purification.

Step 3: 3-(5-(5-((2H-tetrazol-5-yl)methyl)-2-methoxybenzyl)-2-amino-6-(((S)-1-(methyl-sulfonyl)heptan -3-yl)amino)pyrimidin-4-yl)-N—((S)-1-(methylthio)heptan-3-yl)propanamide To a stirred solution of 3-(5-(5-((2H-tetrazol-5-yl) methyl)-2-methoxybenzyl)-2-amino -6-(((S)-1-(methylthio) heptan-3-yl)amino)pyrimidin-4-yl)-N—((S)-1-(methylthio) heptan-3-yl)propanamide (1.0 eq), 1:1:1 THF/MeOH/$H_2O$ (0.02M) at 0° C. was added Oxone (2.0 eq). The resulting mixture was stirred at 0° C. for 3 hr before quenching with saturated aq. $Na_2S_2O_3$. The mixture was partitioned between EA/water. The organic layer was dried over $Na_2SO_4$ and concentrated to give the title compound.

Step 4: (S)-3-(5-(5-((2H-tetrazol-5-yl)methyl)-2-methoxybenzyl)-2-amino-6-((1-(methylsulfonyl) heptan-3-yl)amino)pyrimidin-4-yl)propanoic acid To a stirred solution of 3-(5-(5-((2H-tetrazol-5-yl) methyl)-2-methoxybenzyl)-2-amino -6-(((S)-1-(methylsulfonyl)heptan-3-yl)amino)pyrimidin-4-yl)-N—((S)-1-(methylthio)heptan-3-yl)propanamide (1.0 eq) in ethylene glycol (0.1M) was added 6 N KOH (10 eq). The resulting mixture was stirred at 150° C. for 48 h. The suspension was diluted with 1:1 MeOH/$H_2O$ and then filtered. The filtrate was purified by prep-HPLC (HCOOH/MeCN/$H_2O$) to give the title compound as a white solid. LC-MS: $[M+H]^+=561.3$. $^1H$ NMR (400 MHz, DMSO) δ 7.02 (d, J=7.3 Hz, 1H), 6.92 (d, J=8.4 Hz, 1H), 6.74 (s, 1H), 6.17 (br, 2H), 6.10 (d, J=8.2 Hz, 1H), 4.23 (m, 1H), 4.01 (s, 2H), 3.83 (s, 3H), 3.67 (s, 2H), 3.09-2.80 (m, 5H), 2.58 (t, J=7.3 Hz, 2H), 2.45-2.40 (m, 2H), 1.97-1.84 (m, 1H), 1.80-1.70 (m, 1H), 1.44-1.31 (m, 2H), 1.17-1.15 (m, 2H), 1.06-1.02 (m, 2H), 0.77 (t, J=7.2 Hz, 3H).

Synthesis Example 3: Synthesis of Compound 2B, (S)-3-(2-amino-5-(5-(carboxymethyl)-2-methoxybenzyl) -6-((1-hydroxyheptan-3-yl)amino)pyrimidin-4-yl)propanoic acid

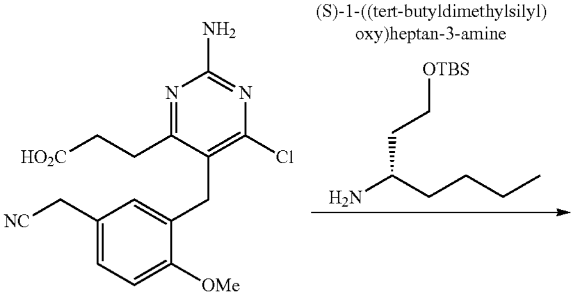

3-(2-amino-6-chloro-5-(5-(cyanomethyl)-2-methoxybenzyl)pyrimidin-4-yl)propanoic acid -continued

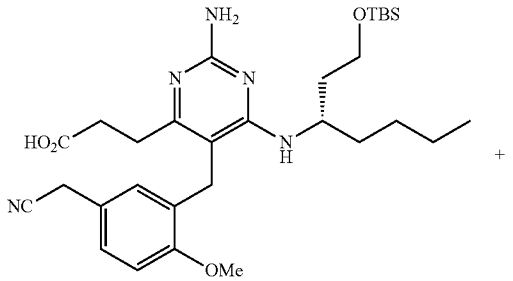

(S)-3-(2-amino-6-((1-((tert-butyldimethylsilyl)oxy)heptan-3-yl)amino)-5-(5-(cyanomethyl)-2-methoxybenzyl)pyrimidin-4-yl)propanoic acid

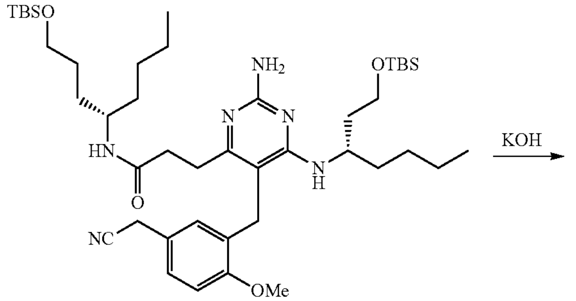

3-(2-amino-6-(((S)-1-((tert-butyldimethylsilyl)oxy)heptan-3-yl)amino)-5-(5-(cyanomethyl)-2-methoxybenzyl)pyrimidin-4-yl)-N-(((S)-1-((tert-butyldimethylsilyl)oxy)heptan-3-yl)propanamide

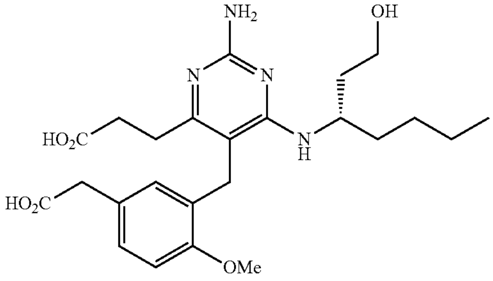

(S)-3-(2-amino-5-(5-(carboxymethyl)-2-methoxybenzyl)-6-((1-hydroxyheptan-3-yl)amino)pyrimidin-4-yl)propanoic acid
Chemical Formula: $C_{24}H_{34}N_4O_6$
Exact Mass: 474.25

Step 1: (S)-3-(2-amino-6-((1-((tert-butyldimethylsilyl)oxy)heptan-3-yl)amino)-5-(5-(cyanomethyl)-2-methoxybenzyl)pyrimidin-4-yl)propanoic acid and 3-(2-amino-6-(((S)-1-((tert-butyldimethylsilyl)oxy)heptan-3-yl)amino)-5-(5-(cyanomethyl)-2-methoxybenzyl)-pyrimidin -4-yl)-N—((S)-1-((tert-butyldimethylsilyl)oxy)heptan-3-yl)propanamide 3-(2-amino-6-chloro-5-(5-(cyanomethyl)-2-methoxybenzyl)pyrimidin-4-yl)propanoic acid (1.0 eq) and neat (S)-1-((tert-butyldimethylsilyl)oxy)heptan-3-amine (3.0 eq) was stirred at 140° C. for 3 hr. The reaction mixture was cooled to rt and used in next step directly without further purification.

Step 2: (S)-3-(2-amino-5-(5-(carboxymethyl)-2-methoxybenzyl)-6-((1-hydroxyheptan-3-yl)amino)pyrimidin-4-yl)propanoic acid The crude mixture from the previous step was dissolved in DMSO (0.2M) and added equal volume of 10N KOH. The mixture was stirred at 130° C. for 2 hr, and then cooled to rt. The upper layer was separated and purified by prep-HPLC (mobile phase: 0.1% FA/$CH_3CN/H_2O$) to give the title compound as a light brown solid. LC-MS: $[M+H]^+$ =475.4. $^1H$ NMR (400 MHz, $CD_3OD$) (57.17 (d, J=8.0 Hz, 1H), 6.95 (s, 1H), 6.91 (d, J=8.0 Hz, 1H), 4.43-4.40 (m, 1H), 3.88 (s, 3H), 3.82-3.76 (m, 2H), 3.43-3.30 (m, 4H), 2.96 (t, J=6.4 Hz, 2H), 2.52 (t, J=6.4 Hz, 2H), 1.80-1.00 (m, 8H), 0.80 (t, J=7.6 Hz, 3H).

Synthesis Example 4: Synthesis of Compound 3B, (S)-3-(5-(5-((2H-tetrazol-5-yl)methyl)-2-methoxybenzyl)-2-amino-6-((1-hydroxyheptan-3-yl)amino)pyrimidin-4-yl)propanoic acid

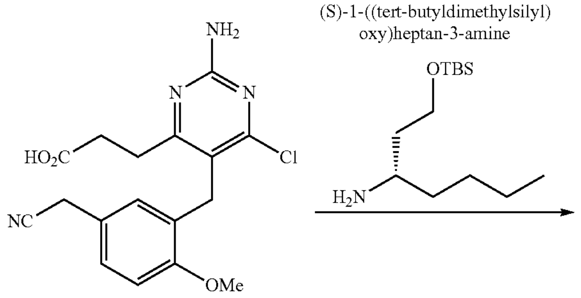

3-(2-amino-6-chloro-5-(5-(cyanomethyl)-2-methoxybenzyl)pyrimidin-4-yl)propanoic acid

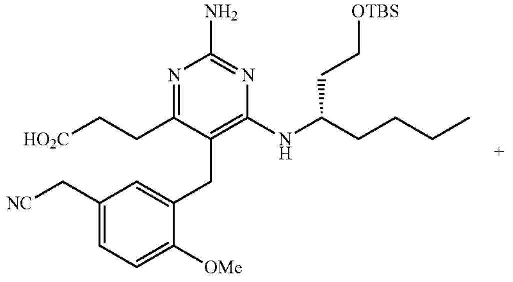

(S)-3-(2-amino-6-((1-((tert-butyldimethylsilyl)oxy)heptan-3-yl)amino)-5-(5-(cyanomethyl)-2-methoxybenzyl)pyrimidin-4-yl)propanoic acid -continued

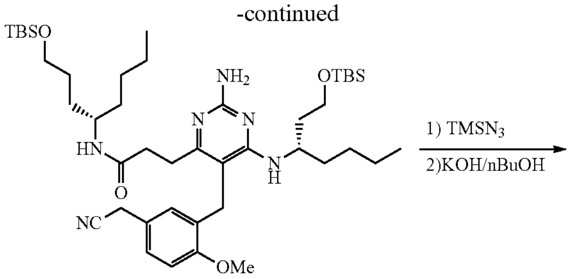

3-(2-amino-6-(((S)-1-((tert-butyldimethylsilyl)oxy)heptan-3-yl)amino)-5-(5-(cyanomethyl)-2-methoxybenzyl)pyrimidin-4-yl)-N-(((S)-1-((tert-butyldimethylsilyl)oxy)heptan-3-yl)propanamide

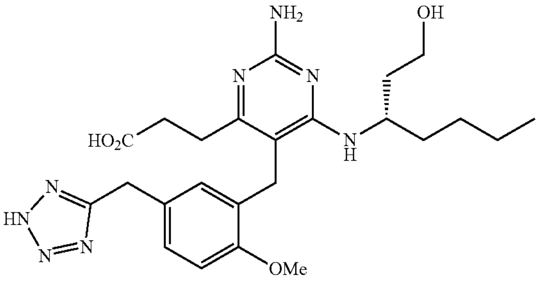

(S)-3-(5-(5-((2H-tetrazol-5-yl)methyl-2-methoxybenzyl)-2-amino-6-((1-hydroxyheptan-3-yl)amino)pyrimidin-4-yl)propanoic acid
Chemical Formula: $C_{24}H_{34}N_8O_4$
Exact Mass: 498.27

Step 1: (S)-3-(2-amino-6-((1-((tert-butyldimethylsilyl)oxy)heptan-3-yl)amino)-5-(5-(cyanomethyl)-2-methoxybenzyl)pyrimidin-4-yl)propanoic acid AND 3-(2-amino-6-(((S)-1-((tert-butyldimethylsilyl)oxy)heptan-3-yl)amino)-5-(5-(cyanomethyl)-2-methoxybenzyl)-pyrimidin -4-yl)-N—((S)-1-((tert-butyldimethylsilyl)oxy)heptan-3-yl)propanamide 3-(2-amino-6-chloro-5-(5-(cyanomethyl)-2-methoxybenzyl)pyrimidin-4-yl)propanoic acid (1.0 eq) and neat (S)-1-((tert-butyldimethylsilyl)oxy)heptan-3-amine (3.0 eq) was stirred at 140° C. for 3 hr. The reaction mixture was cooled to rt and used in next step directly without further purification.

Step 2: (S)-3-(5-(5-((2H-tetrazol-5-yl)methyl)-2-methoxybenzyl)-2-amino-6-((1-hydroxyheptan-3-yl)amino)pyrimidin-4-yl)propanoic acid To the crude mixture from the previous step (1.0 eq) in dioxane (0.14M) was added $TMSN_3$ (2.9 eq) and $Bu_2SnO$ (1.5 eq) and heated in a sealed tube at 100° C. for 6 hr. The reaction mixture was cooled to rt and added 10N KOH (35 eq) and equal volume of n-BuOH. The reaction was heated at 130° C. for 3 hr. The solid was filtered off, the filtrate was concentrated and purified by prep-HPLC (mobile phase: 0.1% $TFA/CH_3CN$) to give the title compound as white solid. LC-MS: $[M+H]^+=499.4$. $^1H$ NMR (400 MHz, $CD_3OD$) δ7.15 (d, J=8.0 Hz, 1H), 6.95-6.90 (m, 2H), 4.43-4.40 (m, 1H), 4.09 (s, 2H), 3.88 (s, 3H), 3.79 (s, 2H), 3.39-3.41 (m, 2H), 2.90 (t, J=6.4 Hz, 2H), 2.51 (t, J=6.0 Hz, 2H), 1.75-1.00 (m, 8H), 0.78 (t, J=7.6 Hz, 3H).

BIOLOGICAL EXAMPLES

Biological Example 1: HEK-TLR7 Assay

This example demonstrates that compounds disclosed herein have in vitro activity against human TLR7.

HEK-Blue™ TLR7 cells were purchased from Invivogen (San Diego, Calif.). The following description was taken from the product information sheet.

"HEK-Blue™ hTLR7 cells are designed for studying the stimulation of human TLR7 (hTLR7) by monitoring the activation of NF-kB. HEK-Blue™ hTLR7 cells were obtained by co-transfection of the hTLR7 gene and an optimized secreted embryonic alkaline phosphatase (SEAP) reporter gene into HEK293 cells. The SEAP reporter gene is placed under the control of the IFN-b minimal promoter fused to five NF-kB and AP-1-binding sites. Stimulation with a TLR7 ligand activates NF-kB and AP-1 which induce the production of SEAP, which is detected by the HEK-Blue™ Detection cell culture medium."

A typical assay protocol involved the following steps:

1. Cells were cultured according to the product information sheet.
2. 10 mM compound stock in DMSO were first diluted to 3 mM and then 3-fold serially diluted using DMSO to afford a 10-pt dilution.
3. 3 µl of the diluted DMSO were added to 57 µl HEK-Blue™ Detection media for a further 20-fold dilution.
4. 10 µl of the diluted compound in assay media were added into 40 µl cell culture (in HEK-Blue™ Detection media) in 384-well plate. Final cell concentration=8,000 cells per well.
5. The plates were incubated at 37° C. in 5% CO2 for 16 h. SEAP was determined using a spectrophotometer at 620-655 nm.

Compounds 1B-3B were measured for HEK-TLR7 activity and compared to AZD8848 and Compound 50. AZD8848 represents the state-of-the-art inhaled TLR7 agonist and is used clinically to treat asthma patients. (Delaney et. al. BMJ Open Respir Res. 2016 Feb. 23; 3(1):e000113).

<u>TLR7 Agonist Comparator Compound, AZD8848</u>

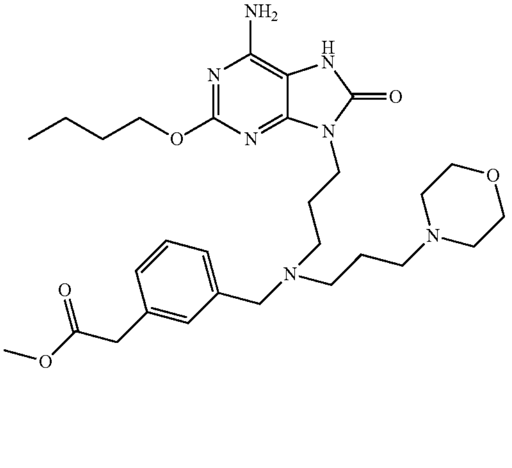

-continued

TLR7 Agonist Comparator Compound 50

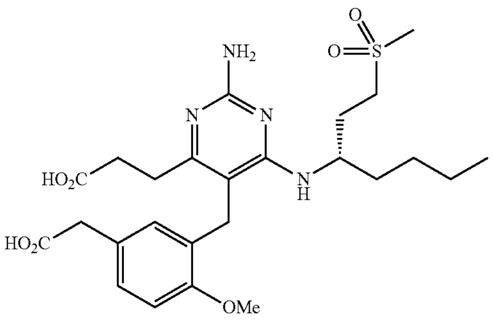

The HEK-TLR7 $EC_{50}$ of compounds 1B-3B ranged from 0.23-0.27 microM. The comparator compound AZD8848 had a HEK-TLR7 $EC_{50}$ of 0.037 microM. The comparator Compound 50 had a HEK-TLR7 $EC_{50}$ of 0.26 microM. These results are summarized below:

| | HEK-TLR7 $EC_{50}$ (microM) |
|---|---|
| Compound 1B | 0.23 |
| Compound 2B | 0.27 |
| Compound 3B | 0.27 |
| AZD8848 (comparator) | 0.037 |
| Compound 50 (comparator) | 0.26 |

Biological Example 2: Formulation Preparation and Solubility Examination

This example demonstrates the improved solubility of TLR7 agonists disclosed herein compared to a known TLR7 agonist used to treat asthma.

Compounds 1B-3B, comparator compound AZD8848, and comparator Compound 50 were suspended in 0.5% carboxy methycellulose in water at 1 mg/mL concentration. The pH was adjusted to 6-7 by adding appropriate amounts of 1N NaOH (Compounds 1B-3B, Compound 50) and 1N HCl (AZD8848). The resulting formulations were vortexed and stored at 4° C. before dosing.

Solutions of compounds 1B-3B and Compound 50 were clear, indicating good solubility compared to AZD8848, which was a turbid suspension. 0.5% carboxy methycellulose in water could be substituted with saline for intranasal administration, and the solubility results are similar.

Biological Example 3: Pharmacodynamic Experiments

This example demonstrates that compounds disclosed herein have high levels of TLR7 target activation in vivo.

IP-10 is a biomarker of TLR7 target activation. Higher production levels of IP-10 is an indication of higher target engagement in vivo. In this study, 3 BALB/c mice per group were dosed intranasally with 60 micrograms of Compound 1B, 2B, 3B, Compound 50 or AZD8848. The test compounds were formulated as a 1 mg/mL solution in 0.5% carboxy methycellulose. Animals were sacrificed after 5 hours. Serum IP-10 concentrations were measured using a commercial ELISA kit purchased from Meso Scale Discovery.

Intranasal dosing of Compounds 1B-3B in mice resulted in higher serum concentrations of IP-10 compared to the comparator compounds (AZD8848 and Compound 50) or vehicle (FIG. 1). The mean IP-10 concentration of in mice dosed with vehicle, AZD8848, or Compound 50 were 17 pg/mL, 96 pg/mL, and 125 pg/mL respectively. Mice dosed with Compounds 1B, 2B, or 3B, in comparison, had a higher mean serum concentration of IP-10 of about 700, 150, and 1300 pg/mL, respectively.

The results demonstrate that mice dosed with Compounds 1B, 2B, or 3B induced a 1.5× to 14× higher concentration of the IP-10 biomarker compared to AZD8848 at the same dose, the state-of-the-art inhaled TLR7 agonist. This is especially surprising since AZD8848 was shown to be an order of magnitude more potent compared to Compounds 1B-3B as reported in the HEK TLR7 in vitro assay described in Biological Example 1.

Compounds 1B and 3B also induced a 5.6× to 10× higher concentration of the IP-10 biomarker compared to Compound 50 at the same dose. This is especially surprising since Compound 50, 1B and 3B were shown to have similar in vitro HEK TLR7 $EC_{50}$ as reported in Biological Example 1.

Biological Example 4: CT26 Metastatic Lung Cancer Model

This experiment demonstrates that treatment with compounds disclosed herein resulted in increased survival time in a lung cancer mice model.

To establish a lung cancer model, 5e5 CT26 cells stably expressing luciferase (Imanis Life Sciences) were injected intravenously into female Balb/c mice on Day 0. On Day 4 post challenge, mice were anesthetized and subjected to whole body bioluminescent imaging (IVIS; Perkin Elmer) to determine tumor burden and in vivo location. Mice with detectable lung tumors were enrolled into the study and randomized such that the average bioluminescence and variance is equivalent amongst all of the study groups. Animals were dosed twice a week for a total of 8 doses with the indicated treatments, and imaged weekly to determine total tumor burden over the course of the treatment.

In this study, intranasal administration of Compounds 1B, 2B, and 3B were administered in combination with anti-PD-L1 to the mice. Anti-PD-L1 is an antibody that functions as a blocking agent against PD-L1 and its protective effects. By blocking PD-L1, anti-PD-L1 permits the tumor cell to be vulnerable to destruction by the immune system. The known TLR7 compound AZD8848 was used as a comparator and administered in combination with anti-PD-L1 to the mice. Compound 50 in combination with anti-PD-L1 was also tested in this study as a comparator. Each treatment group contained 10 mice.

Figure 2:
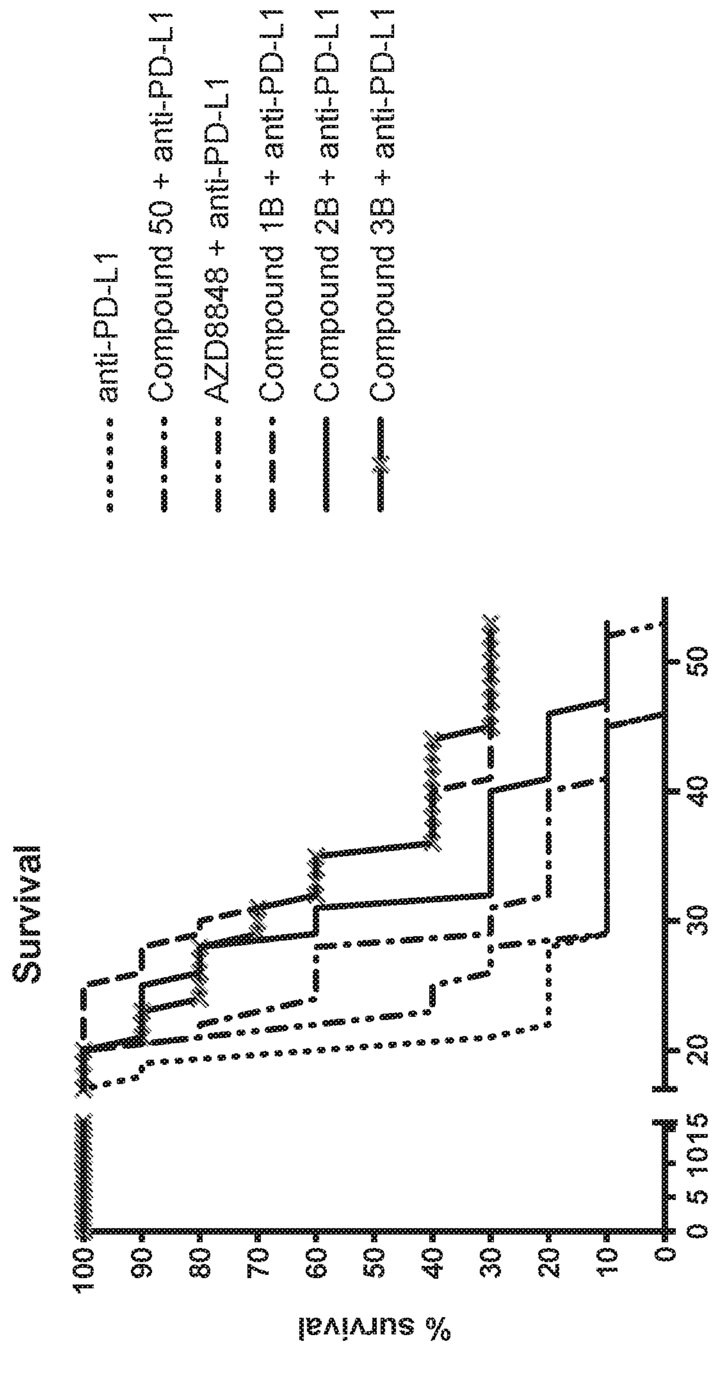
FIG. 2 depicts a line graph comparing the % survival of groups of BALB/C mice with lung tumors treated with anti-PD-L1, or anti-PD-L1 in combination with Compound 50, AZD8848, Compound 1A, Compound 2B, or Compound 3B over a period of about 50 days from the start of treatment.

The median survival time of mice subjects treated with vehicle or anti-PD-L1 was 21 days (FIG. 2). The median survival time of mice treated with anti-PD-L1 in combination with AZD8848 was 23 days. The median survival time for mice treated with anti-PD-L1 in combination with Compound 50 was 29 days. Compared to mice treated with anti-PD-L1, anti-PD-L1 in combination with AZD8848 or Compound 50 were not statistically significant. Surprisingly, Compound 1B, 2B, and 3B extended median survival to 36 days ($p<0.01$), 32 days ($p<0.05$), and 36 days ($p<0.01$), respectively. Thus, intranasal administration of compounds disclosed herein in combination with anti-PD-L1 resulted in longer survival of the mice in comparison to mice treated with only vehicle, anti-PD-L1 alone, AZD8848 (the comparator compound) in combination with anti-PD-L1, or Compound 50 (another comparator compound) in combination with anti-PD-L1. The longer survival time is a surprising result that cannot be achieved with AZD8848, which was developed for inhalation administration. This result is especially surprising since AZD8848 was shown to have a lower in vitro HEK TLR7 $EC_{50}$ than Compounds 1B-3B as reported in Biological Example 1. The longer survival time is also a surprising result that cannot be achieved with Compound 50, a structurally similar analog from WO2018/106606. This result is especially surprising since Compound 50 and Compounds 1B -3B were shown to have similar $EC_{50}$ activity in the HEK TLR7 assay as reported in Biological Example 1.

Figure 3:
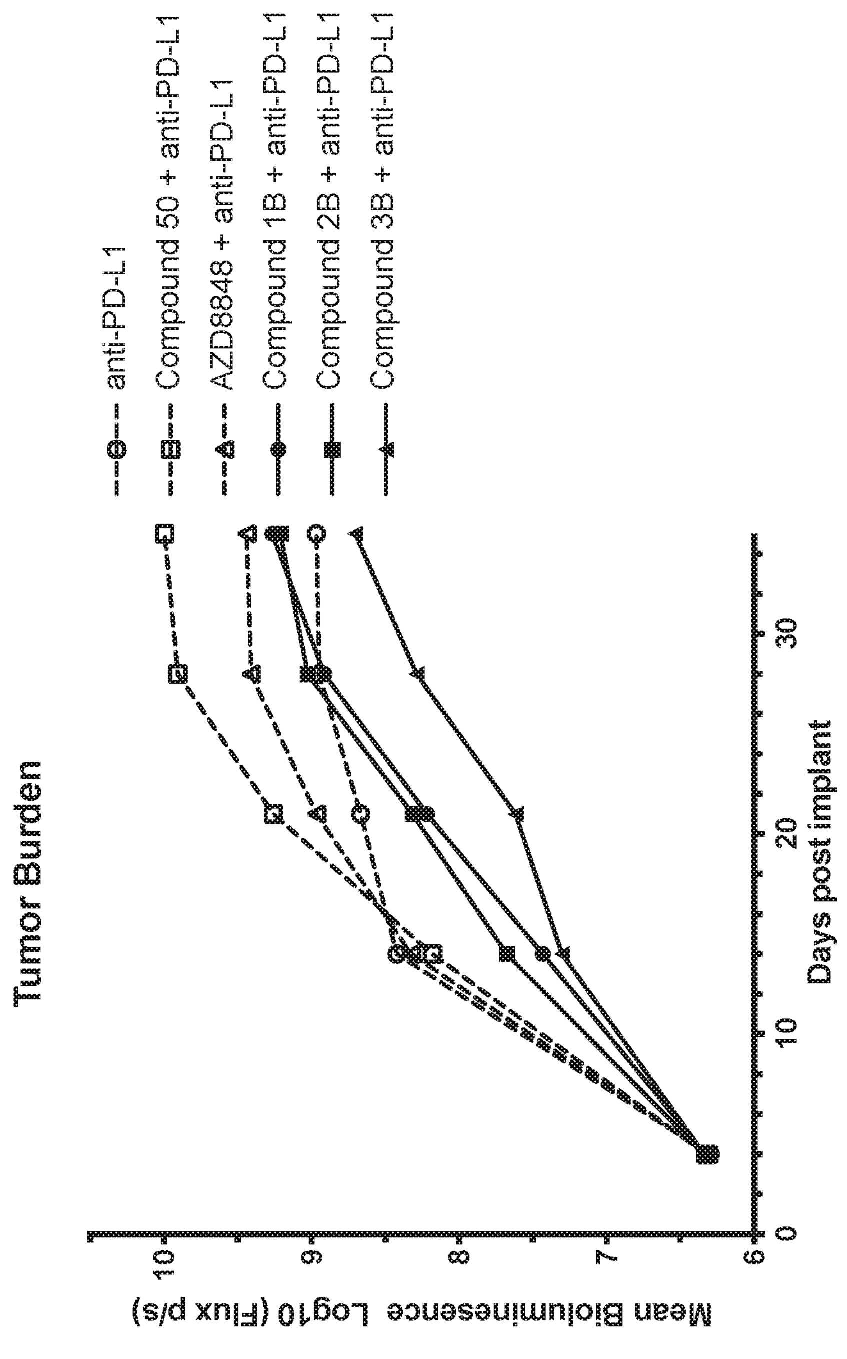
FIG. 3 depicts a line graph of mean bioluminescence detected in BALB/C mice with lung tumors treated with anti-PD-L1, or anti-PD-L1 in combination with Compound 50, AZD8848, Compound 1A, Compound 2B, or Compound 3B over a period of over 30 days from injection with the tumor cells.

In addition, the tumor burden in mice as measured by bioluminescence imaging was measured over the course of treatment. The mean bioluminescence associated with the administration of Compounds 1B, 2B, or 3B was lower than measurements of the mice treated with anti-PD-L1, or the combination of anti-PD-L1 with Compound 50, or AZD8848 for more than 20 days after injection with the tumor cells, FIG. 3. This suggests the use of Compounds 1B, 2B, or 3B in combination with anti-PD-L1 slows the growth of tumor cells compared to treatment with anti-PD-L1, or the combination of anti-PD-L1 with Compound 50, or AZD8848. The reduced tumor burden result is consistent with the increased median survival rates discussed above.

EQUIVALENTS

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

We claim:

1. A compound having the structure of Formula (Ib), or a pharmaceutically acceptable salt thereof, (Ib)

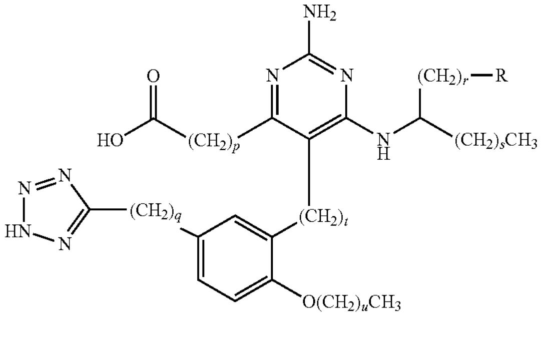

wherein R is selected from the group consisting of —OH, —$SO_2CH_3$, —$NH_2$, —NHAc, and

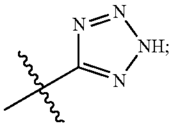 [SMILES: *c1nn[nH]n1]

and p, q, r, s, t, and u are independently selected from zero to four.

2. The compound of claim 1, or a pharmaceutically acceptable salt thereof, wherein p is 2 and q is 1.

3. The compound of claim 1, or a pharmaceutically acceptable salt thereof, wherein R is —OH.

4. The compound of claim 1, or a pharmaceutically acceptable salt thereof, wherein R is —$SO_2CH_3$.

5. The compound of claim 1, or a pharmaceutically acceptable salt thereof, wherein the compound is a single enantiomer.

6. The compound of claim 1, or a pharmaceutically acceptable salt thereof, selected from the group consisting of:

1B

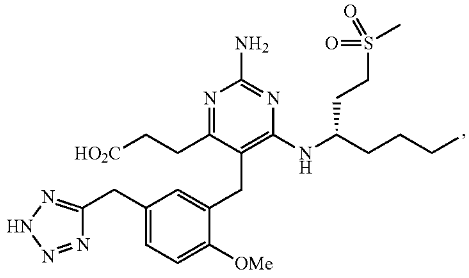

3B

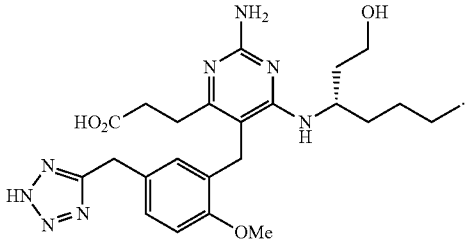

7. A pharmaceutical composition comprising a compound of claim 1, or a pharmaceutically acceptable salt thereof, and a pharmaceutically acceptable carrier.

8. The pharmaceutical composition of claim 7, wherein the pharmaceutically acceptable carrier is carboxy methylcellulose, saline, water, or another aqueous solution.

9. The pharmaceutical composition of claim 7, comprising 0.1%-5% carboxy methylcellulose in water.

10. The pharmaceutical composition of claim 7, wherein the pharmaceutical composition is formulated for inhalation.

* * * * *